(12) United States Patent
Sonderegger et al.

(10) Patent No.: US 10,080,846 B2
(45) Date of Patent: Sep. 25, 2018

(54) SELF-INJECTION DEVICE

(71) Applicant: Becton, Dickinson and Company, Franklin Lakes, NJ (US)

(72) Inventors: Ralph Sonderegger, Farmington, UT (US); Jason Alexander, Lehi, UT (US); Corey Christensen, Salt Lake City, UT (US); Ryan George, Livermore, CA (US); J'Lynn Ingleby, Salt Lake City, UT (US); Patty Chase, Sandy, UT (US); Curt Bingham, Hyde Park, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 98 days.

(21) Appl. No.: 15/380,470

(22) Filed: Dec. 15, 2016

(65) Prior Publication Data

US 2017/0095614 A1    Apr. 6, 2017

Related U.S. Application Data

(62) Division of application No. 13/516,559, filed as application No. PCT/US2009/006570 on Dec. 16, 2009, now Pat. No. 9,555,187.

(51) Int. Cl.
| | |
|---|---|
| *A61M 5/315* | (2006.01) |
| *A61M 37/00* | (2006.01) |
| *A61M 5/142* | (2006.01) |
| *A61M 5/20* | (2006.01) |
| *A61M 5/162* | (2006.01) |

(Continued)

(52) U.S. Cl.
CPC ........ *A61M 5/3157* (2013.01); *A61M 5/1452* (2013.01); *A61M 5/14248* (2013.01); *A61M 5/1626* (2013.01); *A61M 5/16813* (2013.01); *A61M 5/2033* (2013.01); *A61M 5/31528* (2013.01); *A61M 5/3204* (2013.01); *A61M 5/3232* (2013.01); *A61M 37/0015* (2013.01); *A61M 2005/14506* (2013.01); *A61M 2005/206* (2013.01); *A61M 2005/3126* (2013.01); *A61M 2037/0023* (2013.01);

(Continued)

(58) Field of Classification Search
CPC .............. A61M 5/3157; A61M 5/2033; A61M 5/1452; A61M 5/31528; A61M 2205/584; A61M 2005/3126; A61M 2005/14506

See application file for complete search history.

(56) References Cited

U.S. PATENT DOCUMENTS

| | | |
|---|---|---|
| 1,779,451 A | 10/1930 | Sponsel |
| 3,048,171 A | 8/1962 | Grau |

(Continued)

FOREIGN PATENT DOCUMENTS

| | | |
|---|---|---|
| CN | 1863564 A | 11/2006 |
| CN | 1863566 | 11/2006 |

(Continued)

*Primary Examiner* — Bradley J Osinski
(74) *Attorney, Agent, or Firm* — Dickinson Wright PLLC

(57) ABSTRACT

A device for delivering a medicament into a patient's body by injection into or through the patient's skin includes a body having a reservoir disposed therein for containing the medicament, an injection needle for penetrating the skin of the patient, the needle having a lumen and communicating with the reservoir, and a pressurizing system for pressurizing the reservoir. The device also includes indicator means visible outside the device for indicating that delivery of the medicament is substantially complete.

9 Claims, 24 Drawing Sheets

(51) Int. Cl.
*A61M 5/145* (2006.01)
*A61M 5/32* (2006.01)
*A61M 5/168* (2006.01)
*A61M 5/31* (2006.01)

(52) U.S. Cl.
CPC . *A61M 2205/581* (2013.01); *A61M 2205/582* (2013.01); *A61M 2205/584* (2013.01)

(56) References Cited

U.S. PATENT DOCUMENTS

| | | | |
|---|---|---|---|
| 3,814,097 A | 6/1974 | Ganderton et al. | |
| 3,964,482 A | 6/1976 | Gerstel et al. | |
| 4,196,732 A | 4/1980 | Wardlaw | |
| 4,258,711 A | 3/1981 | Tucker et al. | |
| 4,316,463 A | 2/1982 | Schmitz et al. | |
| 4,340,048 A | 7/1982 | Eckenhoff | |
| 4,424,911 A | 1/1984 | Resnick | |
| 4,525,164 A | 6/1985 | Loeb et al. | |
| 4,552,561 A | 11/1985 | Eckenhoff et al. | |
| 4,610,672 A | 9/1986 | Ewalt et al. | |
| 4,634,427 A | 1/1987 | Hannula et al. | |
| 4,664,654 A | 5/1987 | Strauss | |
| 4,772,263 A | 9/1988 | Dorman et al. | |
| 4,781,688 A | 11/1988 | Thoma et al. | |
| 4,886,499 A | 12/1989 | Cirelli et al. | |
| 4,921,475 A | 5/1990 | Sibalis | |
| 4,998,918 A | 3/1991 | Mimura | |
| 5,011,477 A | 4/1991 | Winchell et al. | |
| 5,045,064 A | 9/1991 | Idriss | |
| 5,090,963 A | 2/1992 | Gross et al. | |
| 5,195,982 A | 3/1993 | Hoenig | |
| 5,248,303 A | 9/1993 | Margolin | |
| 5,250,023 A | 10/1993 | Lee et al. | |
| 5,279,544 A | 1/1994 | Gross et al. | |
| 5,316,013 A | 5/1994 | Striebel | |
| 5,527,288 A | 6/1996 | Gross et al. | |
| 5,554,131 A | 9/1996 | Lacivita | |
| 5,649,910 A | 7/1997 | Kriesel et al. | |
| 5,656,032 A | 8/1997 | Kriesel et al. | |
| 5,693,018 A | 12/1997 | Kriesel et al. | |
| 5,716,343 A | 2/1998 | Kriesell et al. | |
| 5,735,818 A | 4/1998 | Kriesel et al. | |
| 5,762,634 A | 6/1998 | Davis | |
| 5,776,103 A | 7/1998 | Kriesel et al. | |
| 5,779,676 A | 7/1998 | Kriesel et al. | |
| 5,781,688 A | 7/1998 | Seong | |
| 5,807,335 A | 9/1998 | Kriesel et al. | |
| 5,814,020 A | 9/1998 | Gross | |
| 5,830,187 A | 11/1998 | Kriesel et al. | |
| 5,848,990 A | 12/1998 | Cirelli et al. | |
| 5,848,991 A | 12/1998 | Gross et al. | |
| 5,858,001 A | 1/1999 | Tsals | |
| 5,858,005 A | 1/1999 | Kriesel | |
| 5,885,250 A | 3/1999 | Kriesel et al. | |
| 5,906,592 A | 5/1999 | Kriesel et al. | |
| 5,921,962 A | 7/1999 | Kriesel et al. | |
| 5,922,353 A | 7/1999 | Magruder | |
| 5,925,017 A | 7/1999 | Kriesel et al. | |
| 5,931,814 A | 8/1999 | Alex et al. | |
| 5,957,891 A | 9/1999 | Kriesel et al. | |
| 5,957,895 A | 9/1999 | Sage et al. | |
| 5,961,492 A | 10/1999 | Kriesel et al. | |
| 5,997,501 A | 12/1999 | Gross et al. | |
| 6,007,518 A | 12/1999 | Kriesel et al. | |
| 6,045,533 A | 4/2000 | Kriesel et al. | |
| 6,068,533 A | 5/2000 | Glickman et al. | |
| 6,074,369 A | 6/2000 | Sage et al. | |
| 6,099,504 A | 8/2000 | Gross et al. | |
| 6,126,637 A | 10/2000 | Kriesel et al. | |
| 6,132,755 A | 10/2000 | Eicher et al. | |
| 6,186,982 B1 | 2/2001 | Gross et al. | |
| 6,261,272 B1 | 7/2001 | Gross et al. | |
| 6,346,095 B1 | 2/2002 | Gross et al. | |
| 6,364,865 B1 | 4/2002 | Lavi et al. | |
| 6,428,517 B1 | 8/2002 | Hochman et al. | |
| 6,478,771 B1 | 11/2002 | Lavi et al. | |
| 6,500,150 B1 | 12/2002 | Gross et al. | |
| 6,530,900 B1 | 3/2003 | Daily et al. | |
| 6,562,000 B2 | 5/2003 | Thompson et al. | |
| 6,569,143 B2 | 5/2003 | Alchas et al. | |
| 6,585,707 B2 | 7/2003 | Cabiri et al. | |
| 6,589,229 B1 | 7/2003 | Connelly et al. | |
| 6,595,956 B1 | 7/2003 | Gross et al. | |
| 6,611,707 B1 | 8/2003 | Prausnitz et al. | |
| 6,641,565 B1 | 11/2003 | Lavi et al. | |
| 6,645,081 B1 | 11/2003 | Salas | |
| 6,645,181 B1 | 11/2003 | Lavi et al. | |
| 6,656,147 B1 | 12/2003 | Gertsek et al. | |
| 6,723,068 B2 | 4/2004 | Lavi et al. | |
| 6,743,211 B1 | 6/2004 | Prausnitz et al. | |
| 6,796,968 B2 | 9/2004 | Ferguson et al. | |
| 6,824,529 B2 | 11/2004 | Gross et al. | |
| 6,843,782 B2 | 1/2005 | Gross et al. | |
| 6,881,203 B2 | 4/2005 | Delmore et al. | |
| 6,890,319 B1 | 5/2005 | Crocker | |
| 6,905,475 B2 | 6/2005 | Hauschild et al. | |
| 6,966,893 B2 | 11/2005 | Holtby et al. | |
| 7,014,625 B2 | 3/2006 | Bengtsson | |
| 7,186,236 B2 | 3/2007 | Gibson et al. | |
| 7,220,244 B2 | 5/2007 | Kriesel et al. | |
| 7,226,439 B2 | 6/2007 | Prausnitz et al. | |
| 7,250,037 B2 | 7/2007 | Shermer et al. | |
| 7,303,549 B2 | 12/2007 | Flaherty et al. | |
| 7,384,413 B2 | 6/2008 | Gross et al. | |
| 7,455,663 B2 | 11/2008 | Bikovsky | |
| 7,530,964 B2 | 5/2009 | Lavi et al. | |
| 7,628,770 B2 | 12/2009 | Ethelfeld et al. | |
| 7,632,247 B2 | 12/2009 | Adams | |
| 7,637,891 B2 | 12/2009 | Wall | |
| 7,670,314 B2 | 3/2010 | Wall et al. | |
| 7,678,079 B2 | 3/2010 | Shermer et al. | |
| 7,713,234 B2 | 5/2010 | Karanzas | |
| 7,766,902 B2 | 8/2010 | Beebe et al. | |
| 7,780,636 B2 | 8/2010 | Radmer et al. | |
| 7,857,131 B2 | 12/2010 | Vedrine | |
| 7,955,297 B2 | 6/2011 | Radmer et al. | |
| 7,955,305 B2 | 6/2011 | Moberg et al. | |
| 7,981,085 B2 | 7/2011 | Ethelfeld et al. | |
| 7,998,117 B2 | 8/2011 | Gross et al. | |
| 8,034,024 B2 | 10/2011 | Rodd et al. | |
| 8,062,253 B2 | 11/2011 | Nielsen et al. | |
| 8,110,209 B2 | 2/2012 | Prestrelski et al. | |
| 8,162,923 B2 | 4/2012 | Adams et al. | |
| 8,167,841 B2 | 5/2012 | Teison-Simony et al. | |
| 8,235,952 B2 | 8/2012 | Wikner | |
| 2002/0095134 A1 | 7/2002 | Pettis et al. | |
| 2003/0109827 A1 | 6/2003 | Lavi et al. | |
| 2003/0135159 A1 | 7/2003 | Daily et al. | |
| 2004/0059316 A1 | 3/2004 | Smedegaard | |
| 2004/0116847 A1 | 6/2004 | Wall | |
| 2005/0065472 A1 | 3/2005 | Cindrich et al. | |
| 2006/0122562 A1 | 6/2006 | Needle et al. | |
| 2007/0021733 A1 | 1/2007 | Hansen et al. | |
| 2007/0049873 A1 | 3/2007 | Hansen et al. | |
| 2007/0129650 A1 | 6/2007 | Freeman et al. | |
| 2007/0156094 A1 | 7/2007 | Safabash et al. | |
| 2007/0225676 A1 | 9/2007 | Prausnitz et al. | |
| 2007/0287960 A1 | 12/2007 | Adams | |
| 2007/0299394 A1 | 12/2007 | Rolfe et al. | |
| 2008/0091139 A1 | 4/2008 | Srinivasan et al. | |
| 2008/0210892 A1 | 9/2008 | Wagner | |
| 2008/0215015 A1 | 9/2008 | Cindrich et al. | |
| 2009/0131860 A1 | 5/2009 | Nielsen | |
| 2010/0100048 A1 | 4/2010 | Nielsen et al. | |
| 2010/0234811 A1 | 9/2010 | Schubert et al. | |
| 2011/0270218 A1 | 11/2011 | Gross et al. | |
| 2011/0275999 A1 | 11/2011 | Gross et al. | |
| 2012/0310173 A1 | 12/2012 | Sonderegger | |
| 2012/0310175 A1 | 12/2012 | Vedrine et al. | |
| 2012/0316506 A1 | 12/2012 | Sonderegger et al. | |
| 2012/0323183 A1 | 12/2012 | Peterson et al. | |

(56) References Cited

U.S. PATENT DOCUMENTS

| | | | |
|---|---|---|---|
| 2013/0006195 A1 | 1/2013 | Sonderegger et al. | |
| 2013/0006196 A1 | 1/2013 | Sonderegger et al. | |
| 2013/0165866 A1 | 6/2013 | Christensen | |

FOREIGN PATENT DOCUMENTS

| | | |
|---|---|---|
| CN | 1901951 A | 1/2007 |
| CN | 101107030 A | 1/2008 |
| CN | 101184519 A | 5/2008 |
| CN | 101262897 A | 9/2008 |
| DE | 4039191 | 11/1991 |
| JP | H07503162 | 4/1995 |
| JP | 2005270579 | 10/2005 |
| JP | 2005538773 | 12/2005 |
| JP | 2006511582 | 4/2006 |
| JP | 2007502169 | 2/2007 |
| JP | 2008521482 | 6/2008 |
| JP | 2009119012 | 6/2009 |
| JP | 2009529380 | 8/2009 |
| JP | 2009536564 | 10/2009 |
| WO | WO-8704631 | 8/1987 |
| WO | WO-9314797 | 8/1993 |
| WO | WO-9513838 | 5/1995 |
| WO | WO-9710012 | 3/1997 |
| WO | WO-9721457 | 6/1997 |
| WO | WO-9741917 | 11/1997 |
| WO | WO-0074763 | 12/2000 |
| WO | WO-02083214 | 10/2002 |
| WO | WO-2005002649 | 1/2005 |
| WO | WO-2005018703 | 3/2005 |
| WO | WO-2008030461 | 3/2008 |
| WO | WO-2008077706 | 7/2008 |
| WO | WO-2008116688 | 10/2008 |
| WO | WO-2009141005 | 11/2009 |
| WO | WO-2009141067 | 11/2009 |
| WO | WO-2010/066592 A2 | 6/2010 |

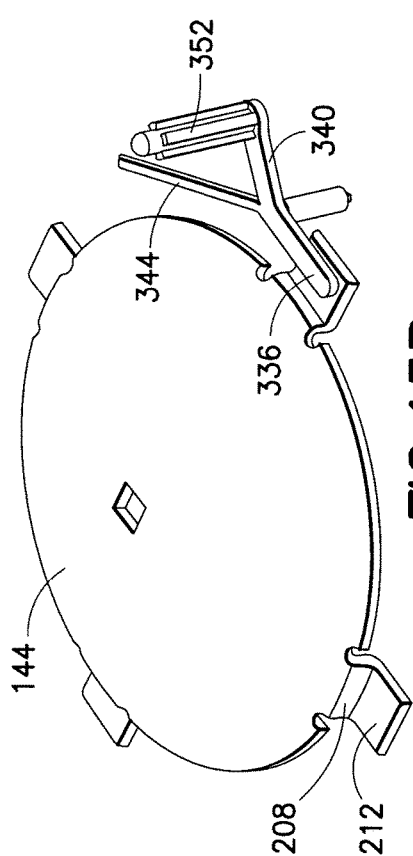
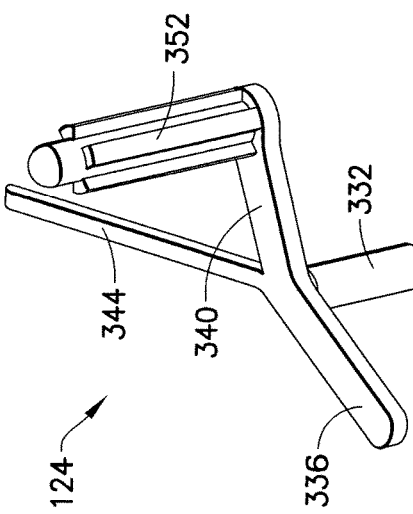
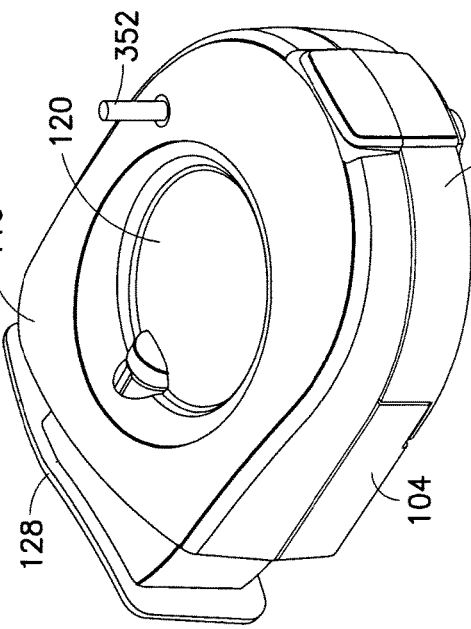
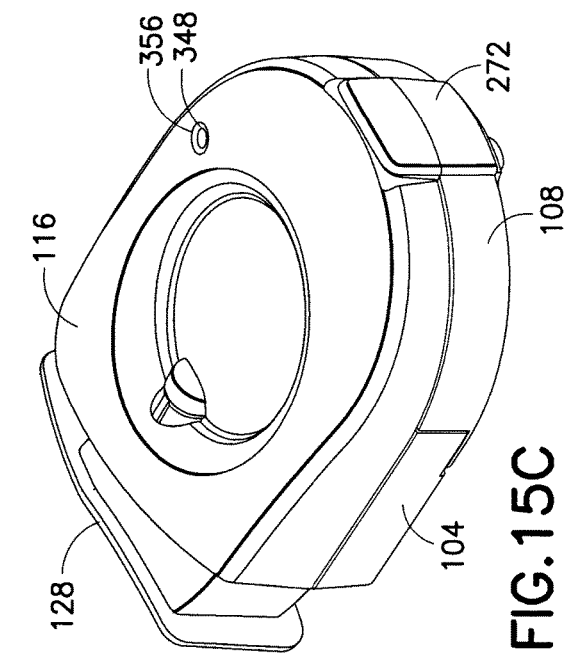

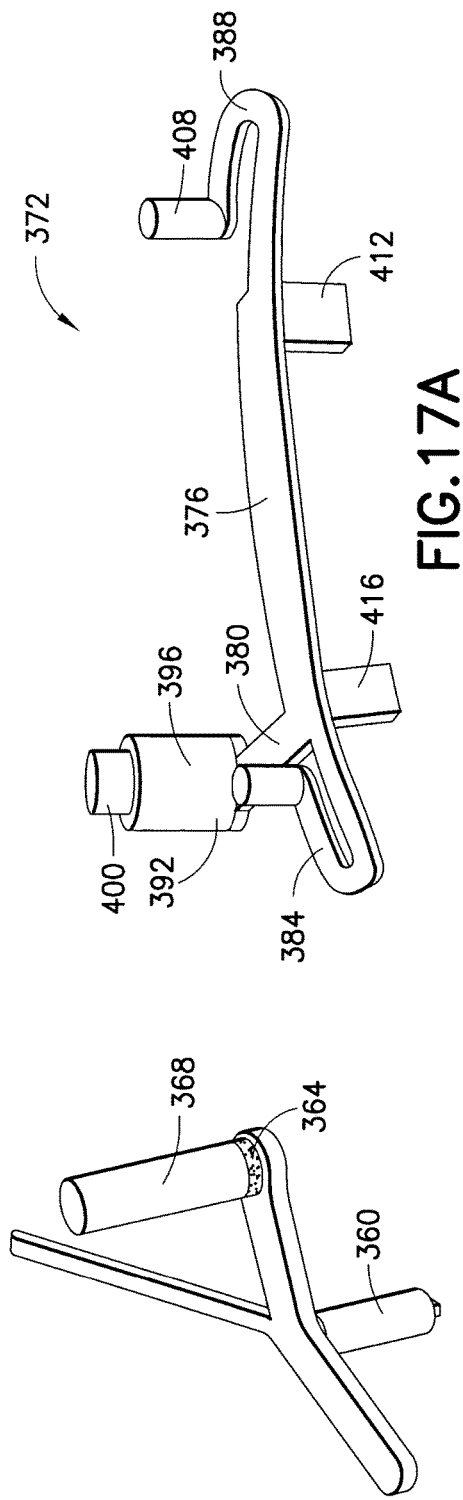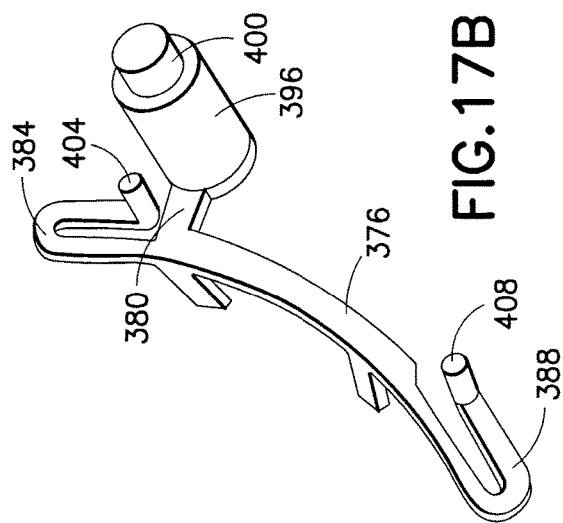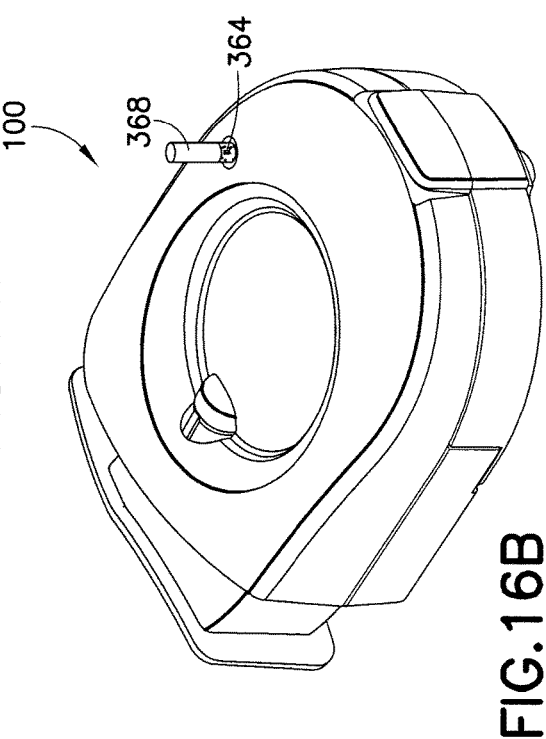

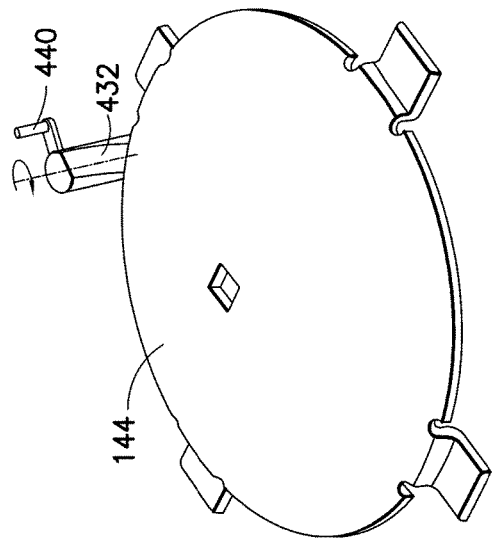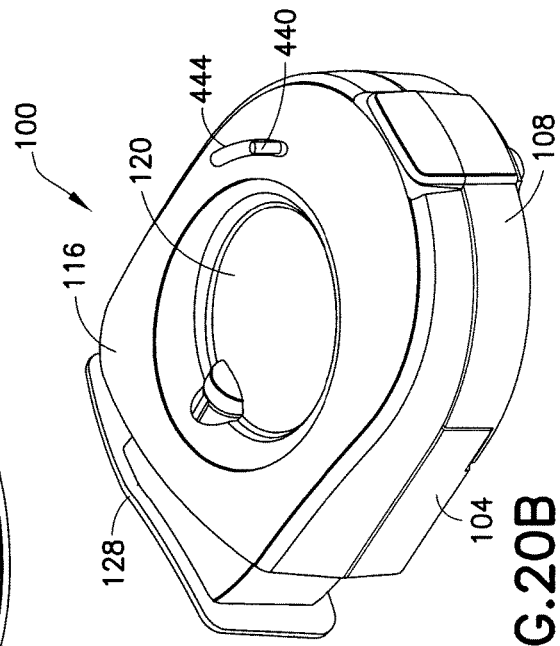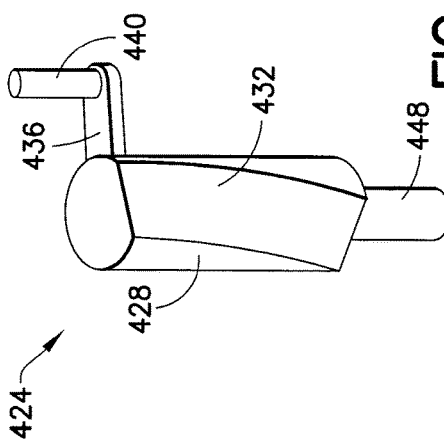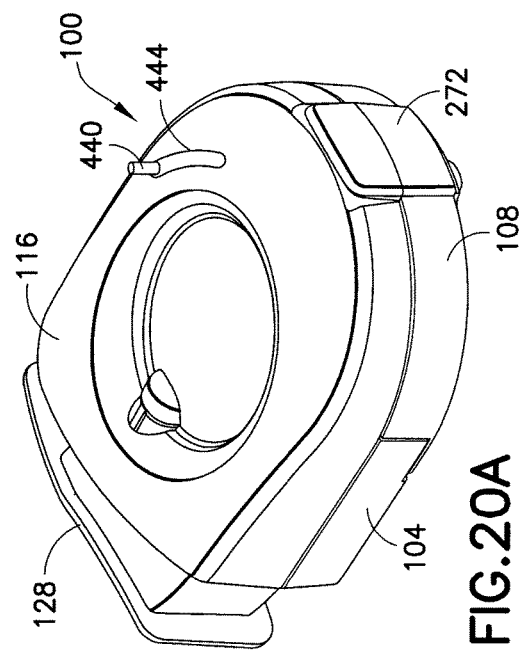

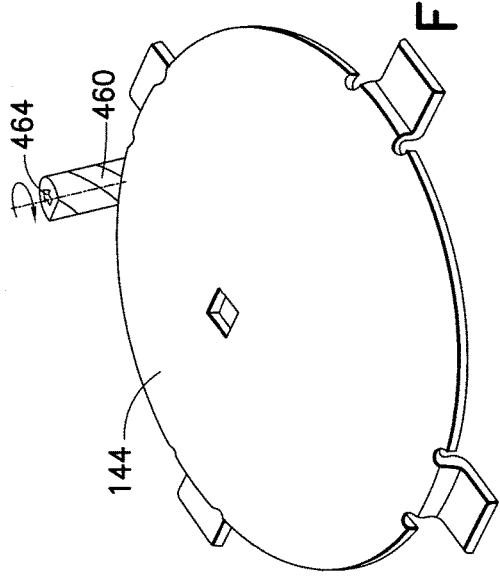
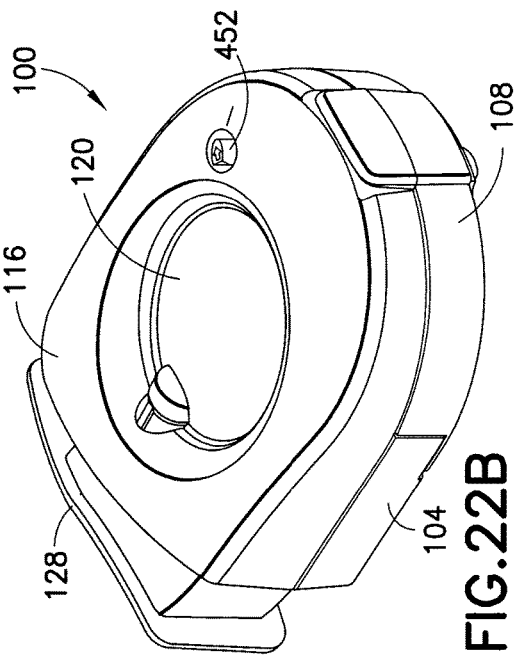
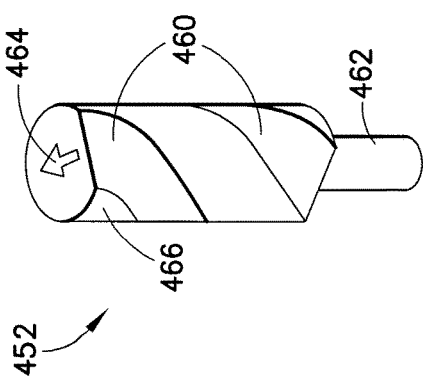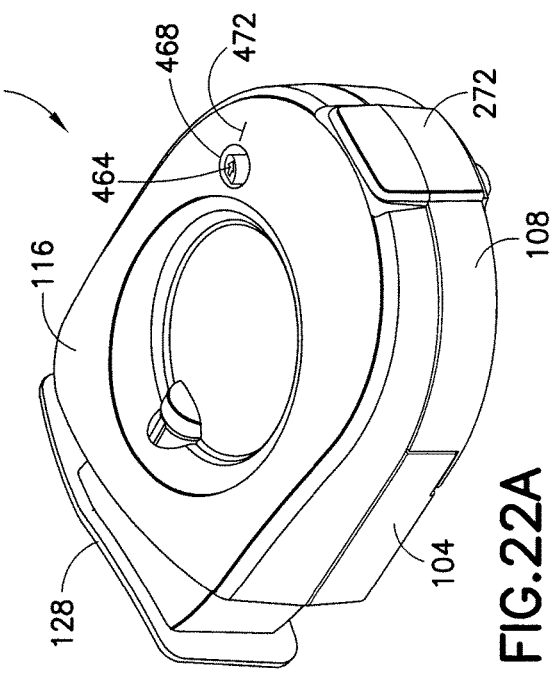

SELF-INJECTION DEVICE

CROSS-REFERENCE TO RELATED APPLICATION

This application is a division of U.S. patent application Ser. No. 13/516,559, filed on Aug. 22, 2012, which is the U.S. national stage under 35 U.S.C. 371 of International Patent Application No. PCT/US2009/006570, filed on Dec. 16, 2009, the disclosures of which are incorporated herein by reference in their entireties.

FIELD OF THE INVENTION

The present invention relates generally to a substance delivery device having improved patient convenience, ease of use, and efficiency. The present invention also relates generally to a patch-like, self-contained substance infusion or self-injection device that can be used to deliver a variety of substances or medications to a patient. More specifically, the present invention relates to a patch-like infusion or self-injection device with an end-of-dose indicator.

BACKGROUND OF THE INVENTION

A large number of people, such as those suffering from conditions such as diabetes, use some form of infusion therapy, such as daily insulin infusions, to maintain close control of their glucose levels. Currently, in the insulin infusion treatment example, there are two principal modes of daily insulin therapy. The first mode includes syringes and insulin pens. These devices are simple to use and are relatively low in cost, but they require a needle stick at each injection typically three to four times per day. The second mode includes infusion pump therapy, which entails the purchase of an expensive pump that lasts for about three years. The high cost (roughly 8 to 10 times the daily cost of syringe therapy) and limited lifetime of the pump are high barriers to this type of therapy. Insulin pumps also represent relatively old technology and are cumbersome to use. From a lifestyle standpoint, moreover, the tubing (known as the "infusion set") that links the pump with the delivery site on the patient's abdomen is very inconvenient and the pumps are relatively heavy, making carrying the pump a burden. From a patient perspective, however, the overwhelming majority of patients who have used pumps prefer to remain with pumps for the rest of their lives. This is because infusion pumps, although more complex than syringes and pens, offer the advantages of continuous infusion of insulin, precision dosing and programmable delivery schedules. This results in closer glucose control and an improved feeling of wellness.

Interest in better therapy is on the rise, accounting for the observed growth in pump therapy and increased number of daily injections. In this and similar infusion examples, what is needed to fully meet this increased interest is a form of insulin delivery or infusion that combines the best features of daily injection therapy (low cost and ease of use) with those of the insulin pump (continuous infusion and precision dosing) and that also avoids the disadvantages of each.

Several attempts have been made to provide ambulatory or "wearable" drug infusion devices that are low in cost and convenient to use. Some of these devices are intended to be partially or entirely disposable. In theory, devices of this type can provide many of the advantages of an infusion pump without the attendant cost and inconvenience. Unfortunately, however, many of these devices suffer from disadvantages including patient discomfort (due to the gauge and/or length of injection needle used), compatibility and interaction between the substance being delivered and the materials used in the construction of the infusion device, and possible malfunctioning if not properly activated by the patient (for example, "wet" injections resulting from premature activation of the device). Difficulties in manufacturing and in controlling needle penetration depth have also been encountered, particularly when short and/or fine-gauge injection needles are used. The possibility of needle-stick injuries to those who come into contact with the used device has also been problematic.

Accordingly, a need exists for an alternative to current infusion devices, such as infusion pumps for insulin, that further provides simplicity in manufacture and use improvements for insulin and non-insulin applications.

SUMMARY OF THE INVENTION

An aspect of the present invention is to provide a patch-like infusion or self-injection device that can be conveniently worn against the skin while providing infusion of a desired substance, and providing minimal discomfort by using one or more microneedles. An additional aspect of the present invention is to provide such an infusion or self-injection device having an end-of-dose indicator.

The foregoing and/or other aspects of the present invention are achieved by providing a device for delivering a medicament into a patient's body by injection into or through the patient's skin, including a body having a reservoir disposed therein for containing the medicament, an injection needle for penetrating the skin of the patient, the needle having a lumen and communicating with the reservoir, and a pressurizing system for pressurizing the reservoir. The device also includes indicator means visible outside the device for indicating that delivery of the medicament is substantially complete.

The foregoing and/or other aspects of the present invention are also achieved by providing a device for delivering a medicament into a patient's body by injection into or through the patient's skin, including a body, a reservoir disposed within the body for containing the medicament, an injection needle for penetrating the skin of the patient and administering the medicament from the reservoir, and a pressurizing system for pressurizing the reservoir. The device also includes an end-of-dose indicator visible outside the device for indicating that delivery of the medicament is substantially complete.

Additional and/or other aspects and advantages of the present invention will be set forth in part in the description that follows and, in part, will be apparent from the description, or may be learned by practice of the invention.

BRIEF DESCRIPTION OF THE DRAWINGS

The above and/or other aspects and advantages of embodiments of the invention will be more readily appreciated from the following detailed description, taken in conjunction with the accompanying drawings, of which:

FIGS. 15A-15D illustrate an end-of-dose indicator and the operation thereof in the infusion device of FIG. 1;

FIGS. 16A and 16B illustrate another end-of-dose indicator and the operation thereof in the infusion device of FIG. 1;

FIGS. 17A and 17B illustrate yet another end-of-dose indicator;

FIGS. 19A and 19B illustrate still another end-of-dose indicator and the operation thereof;

FIGS. 20A and 20B indicate the operation of the end-of-dose indicator of FIG. 19A in the infusion device of FIG. 1;

FIGS. 21A and 21B illustrate still another end-of-dose indicator and the operation thereof;

FIGS. 22A and 22B indicate the operation of the end-of-dose indicator of FIG. 21A in the infusion device of FIG. 1;

DETAILED DESCRIPTION OF EXEMPLARY EMBODIMENTS

Figure 1:
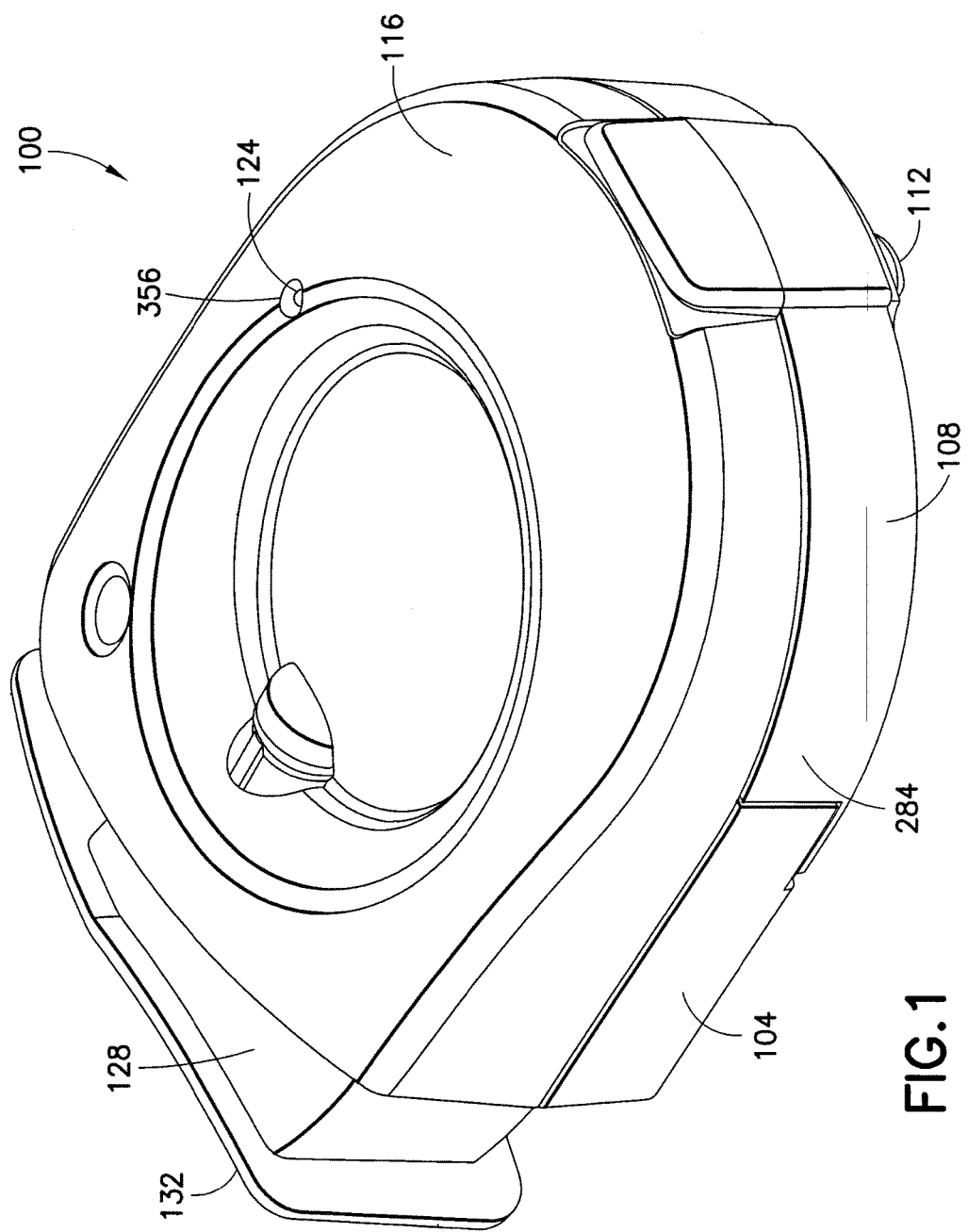
FIG. 1 illustrates a perspective view of an embodiment of a patch-like infusion or self-injection device in a pre-activated state prior to activation.
Figure 2:
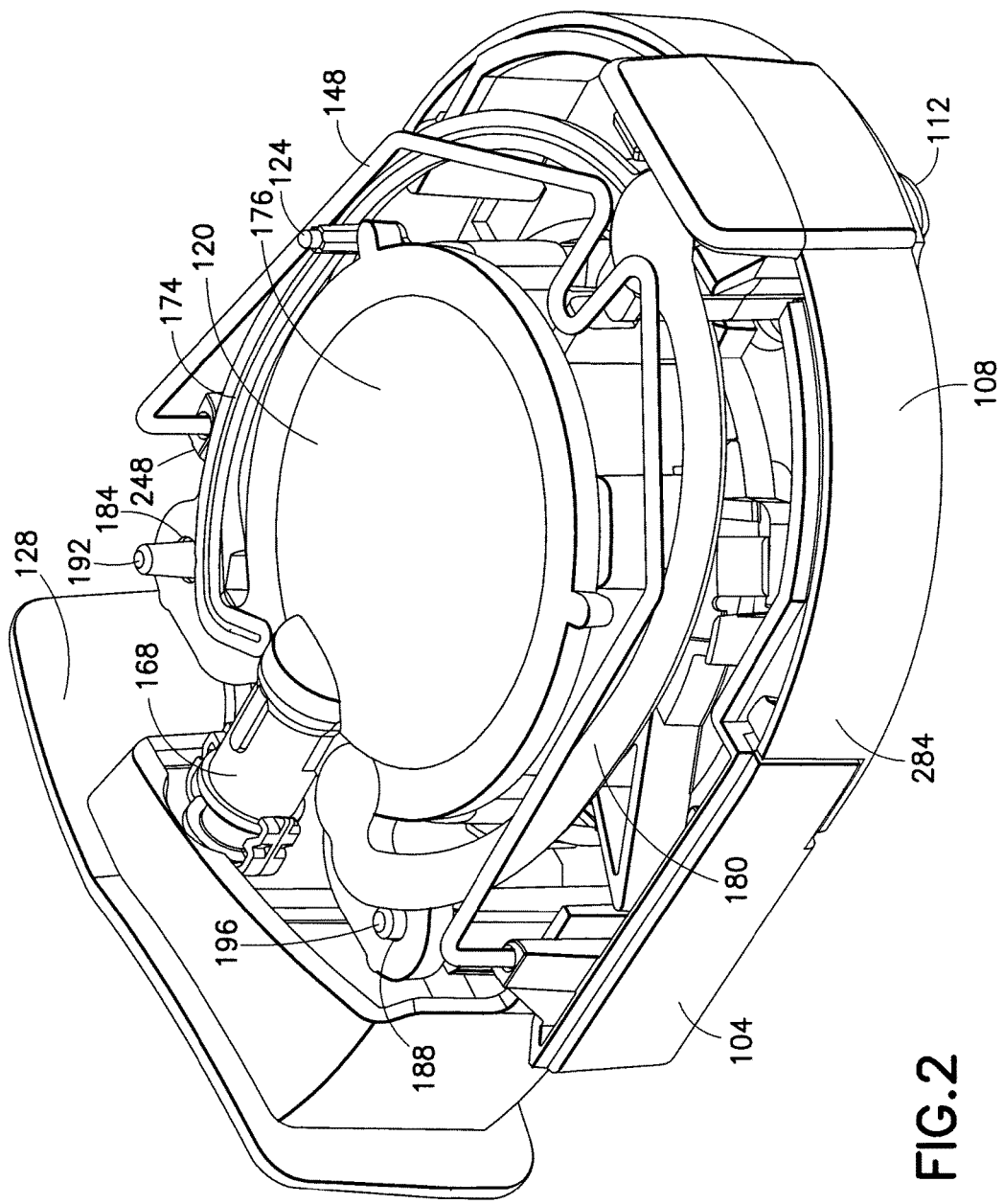
FIG. 2 illustrates a partially exploded view of the infusion device of FIG. 1 in the pre-activated state.

Reference will now be made in detail to embodiments of the present invention, examples of which are illustrated in the accompanying drawings, wherein like reference numerals refer to the like elements throughout. The embodiments described exemplify the present invention by referring to the drawings.

The embodiments of the present invention described below can be used as a convenient, patch-like infusion or self-injection device 100 to deliver a pre-measured dose of a substance, such as a liquid drug or medication, to a patient over a period of time or all at once. The device is preferably provided to the end user in a pre-filled condition, that is, with the drug or medication already in the device reservoir. Though the patch-like infusion or self-injection device 100 (shown, for example, in FIG. 1) described herein can be employed by a patient and/or a caregiver, for convenience, a user of the device is hereinafter referred to as a "patient." Additionally, for convenience, terms such as "vertical" and "horizontal" and "top" and "bottom" are employed to represent relative directions with respect to an infusion device 100 disposed on a horizontal surface. It will be understood, however, that the infusion device 100 is not limited to such an orientation, and that the infusion device 100 may be employed in any orientation. Further, the alternative use of the terms "infusion device" and "self-injection device" to describe devices embodying the present invention is not intended in a limiting sense. Infusion devices that do not have a self-injection capability are within the scope of the present invention, as are self-injection devices that do not carry out continuous infusion. For convenience, but not by way of limitation, the term "infusion device" is used in the description that follows.

The patch-like infusion device 100 of FIG. 1 is self-contained and is attached to the skin surface of the patient by adhesive disposed on a bottom surface of the infusion device 100 (as will be described in greater detail below). Once properly positioned and activated by the patient, the pressure of a released spring on a flexible reservoir within the device can be used to empty the contents of the reservoir through one or more patient needles (for example, microneedles) via a needle manifold. The substance within the reservoir is then delivered through the skin of the patient by the microneedles, which are driven into the skin. It will be understood that other embodiments are possible in which the spring is replaced with a different type of stored energy device, which may be mechanical, electrical and/or chemical in nature.

As will be appreciated by one skilled in the art, there are numerous ways of constructing and using the patch-like infusion device 100 disclosed herein. Although reference will be made to the embodiments depicted in the drawings and the following descriptions, the embodiments disclosed herein are not meant to be exhaustive of the various alternative designs and embodiments that are encompassed by the disclosed invention. In each disclosed embodiment, the device is referred to as an infusion device, but the device may also inject substances at a much faster (bolus) rate than is commonly accomplished by typical infusion devices. For example, the contents can be delivered in a period as short as several seconds or as long as several days.

Figure 5:
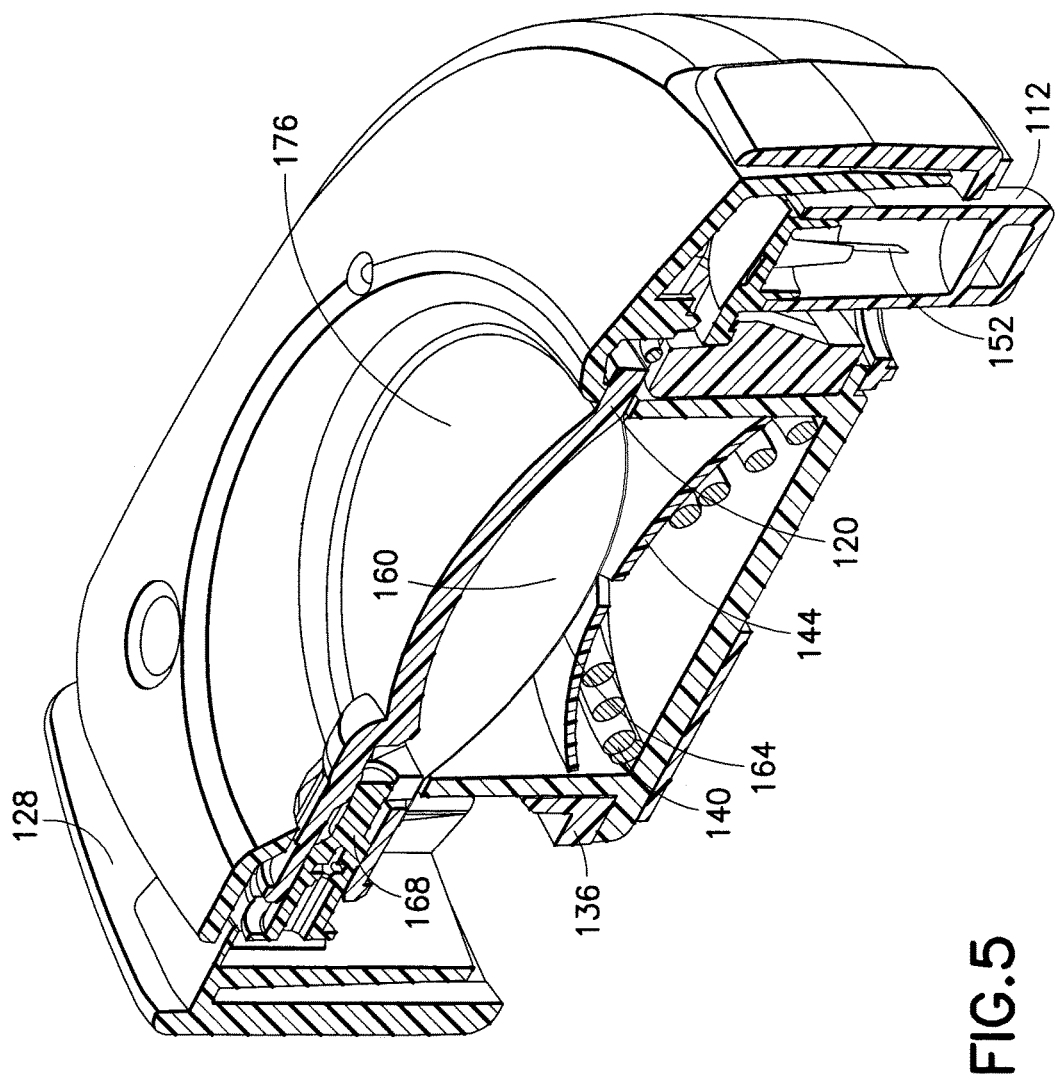
FIG. 5 illustrates a cross-sectional view of the infusion device of FIG. 1 in the pre-activated state.
Figure 6:
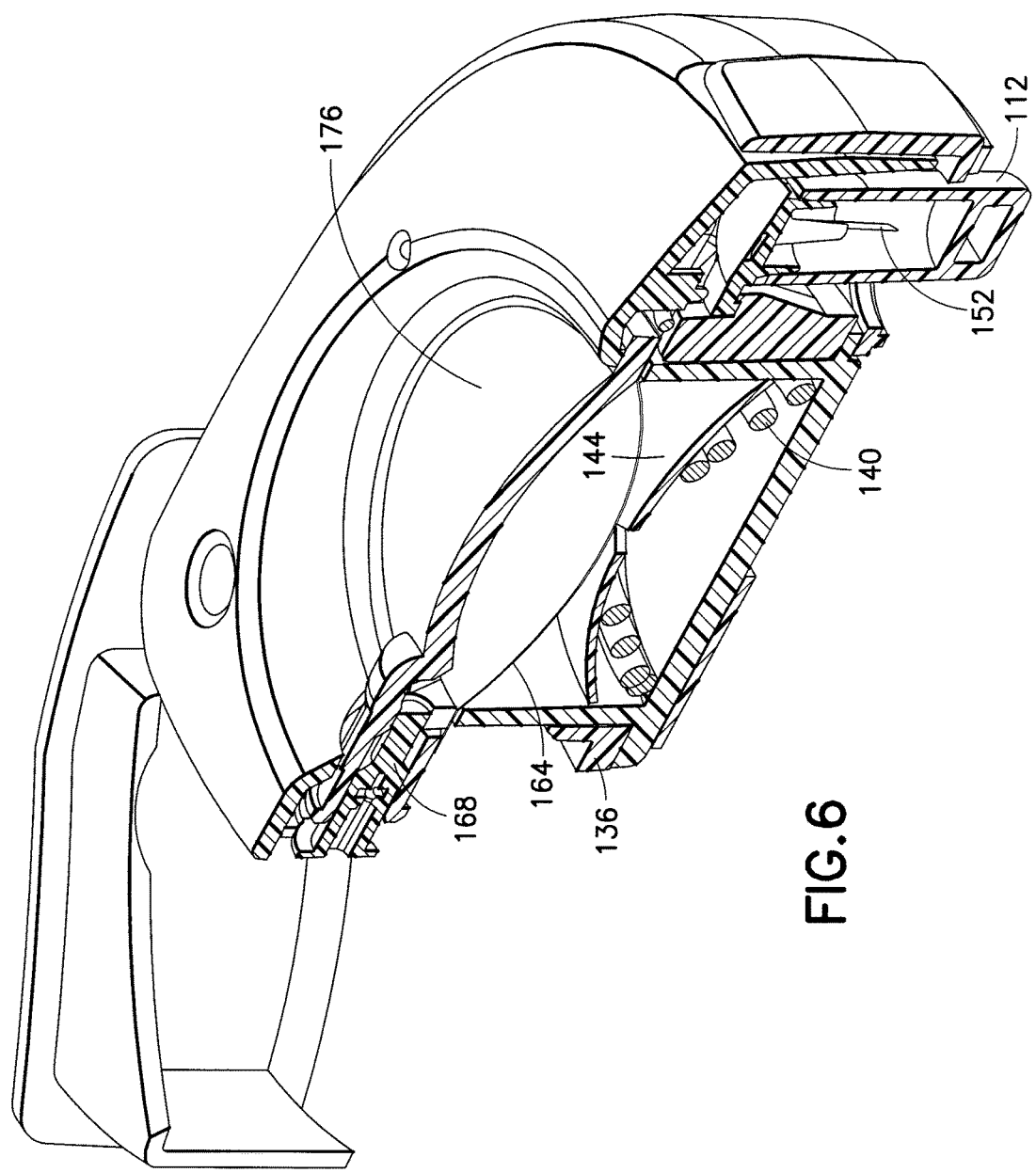
FIG. 6 illustrates a cross-sectional view of the infusion device of FIG. 1 in the pre-activated state with the activator button rotated away.
Figure 7:
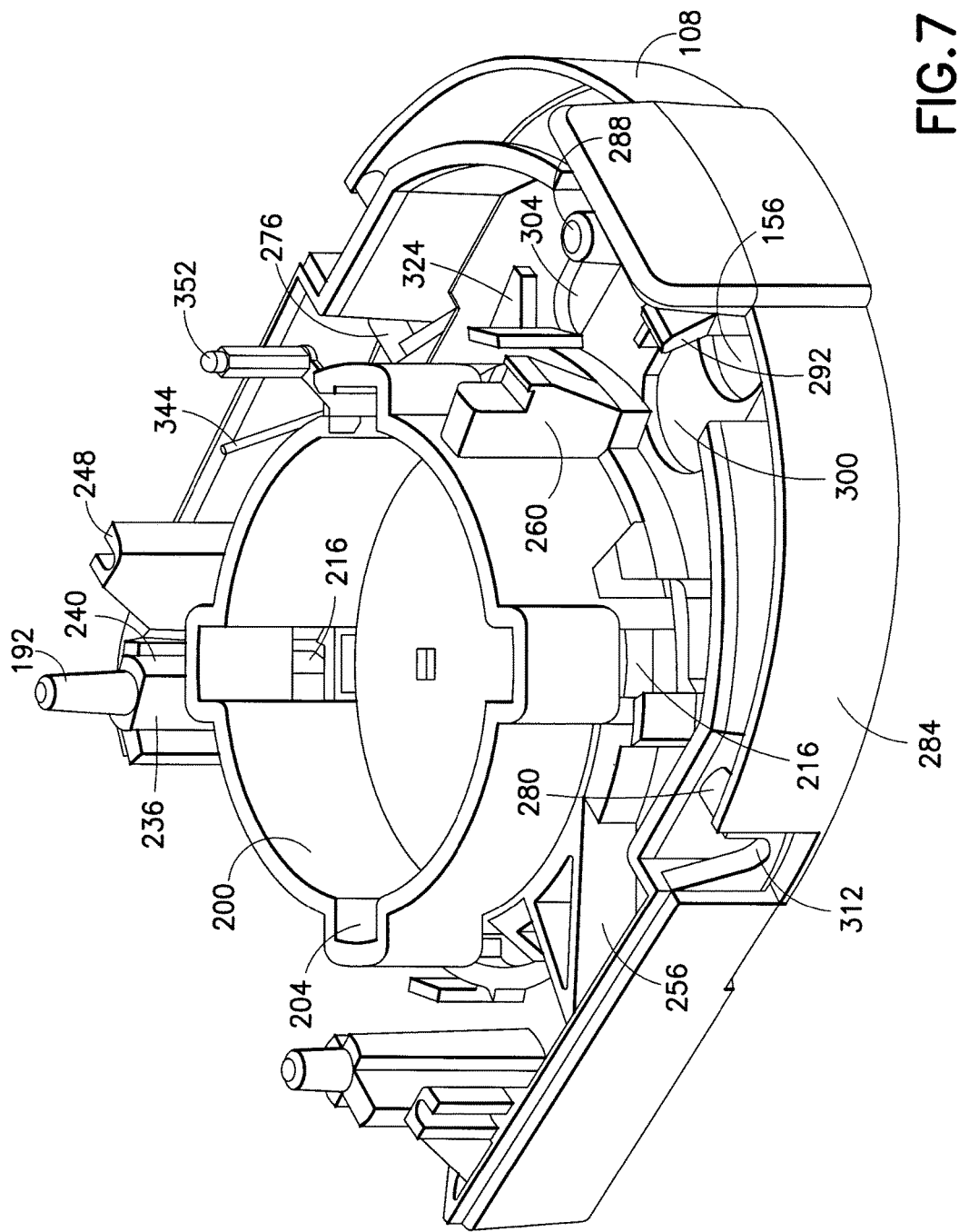
FIG. 7 illustrates a partially exploded view of the infusion device of FIG. 1 during installation of a safety mechanism.
Figure 8:
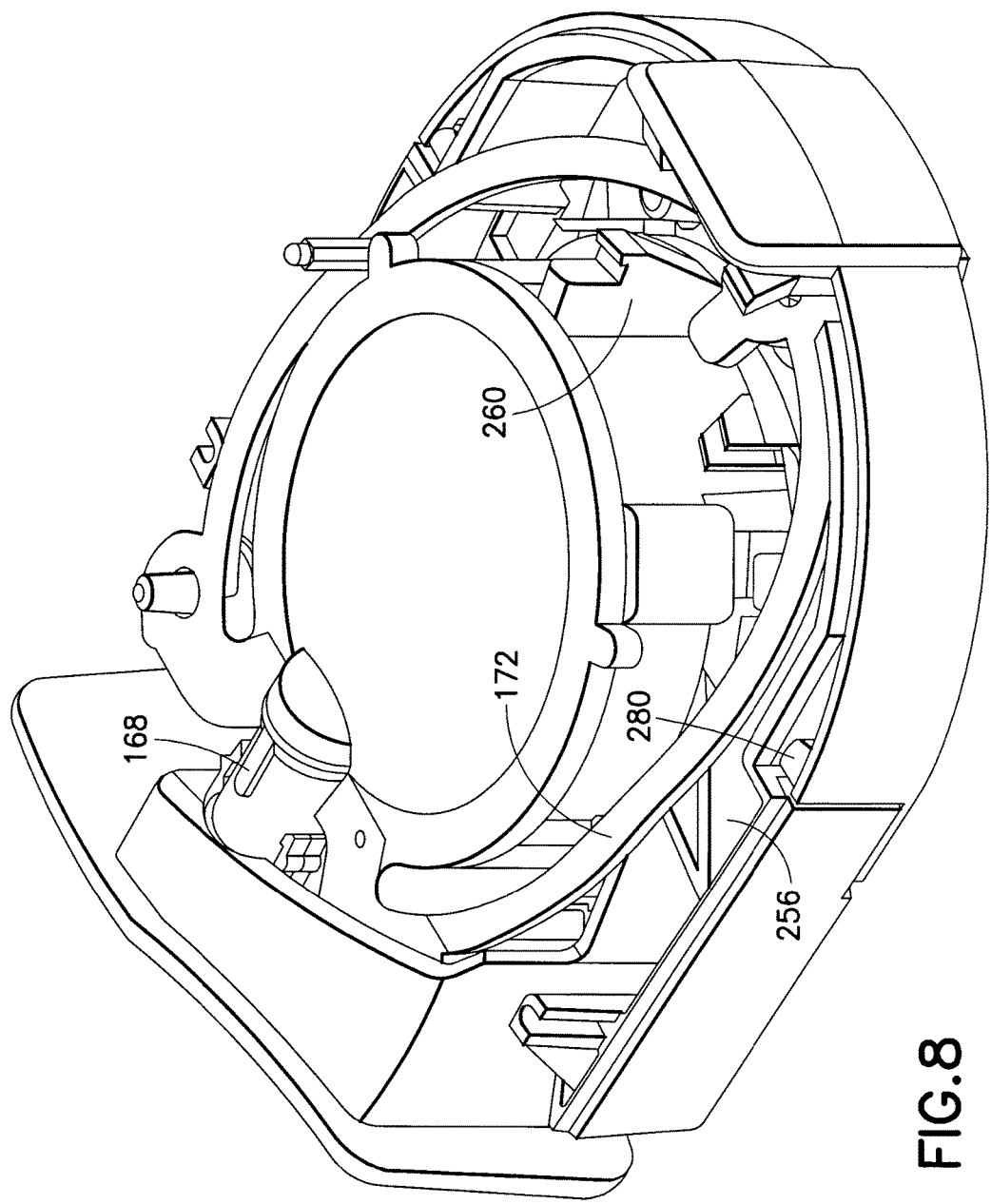
FIG. 8 illustrates a partially exploded view of the infusion device of FIG. 1 subsequent to activation.
Figure 9:
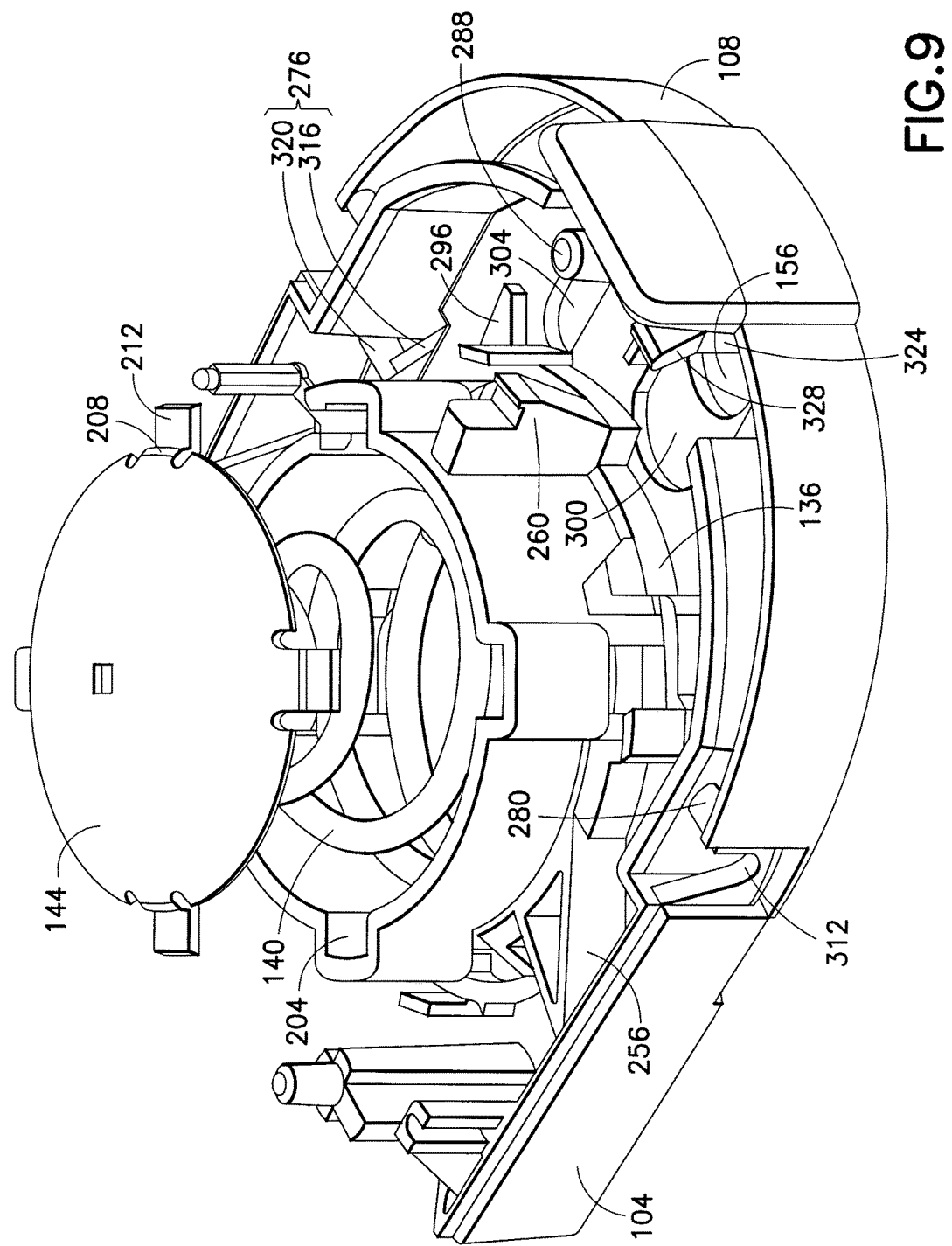
FIG. 9 illustrates a more fully exploded view of the infusion device of FIG. 1 subsequent to activation.
Figure 10:
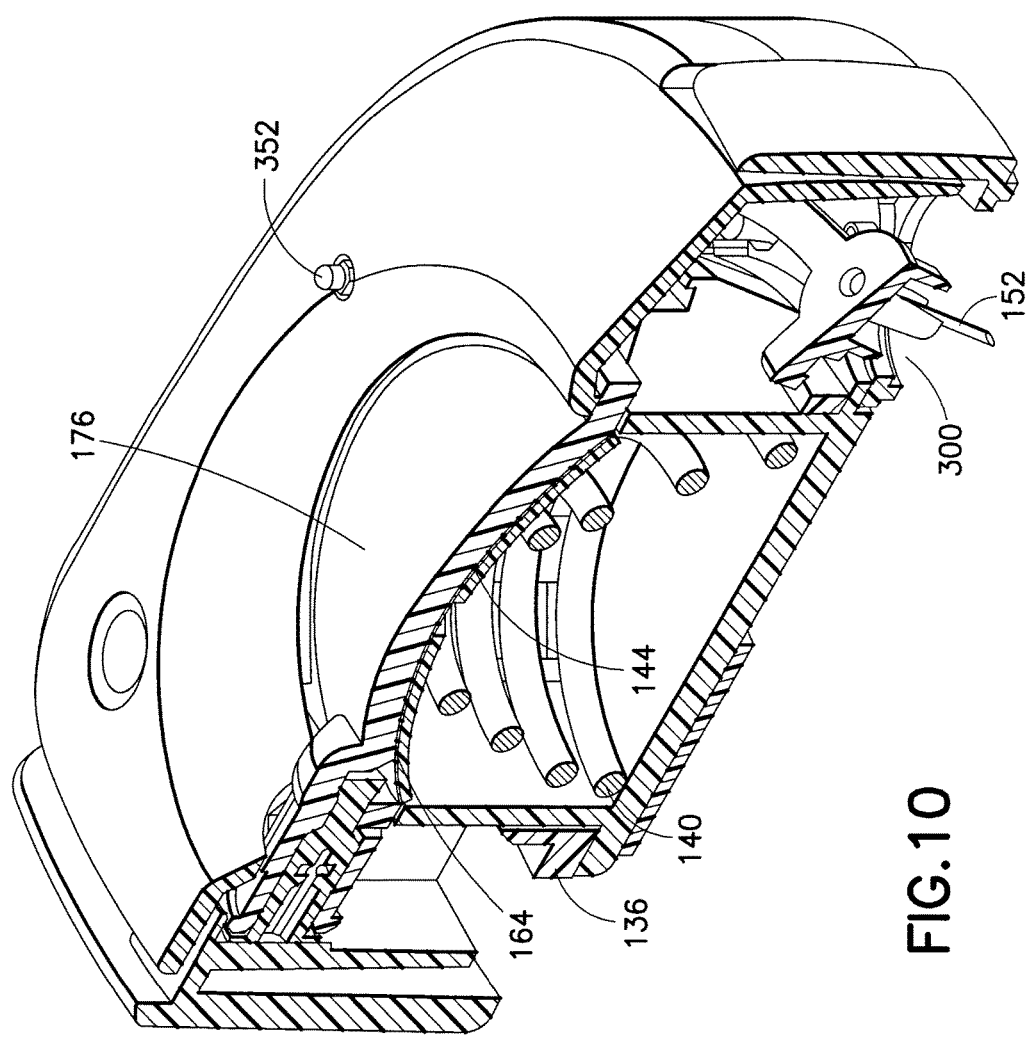
FIG. 10 illustrates a cross-sectional view of the infusion device of FIG. 1 subsequent to activation.
Figure 11:
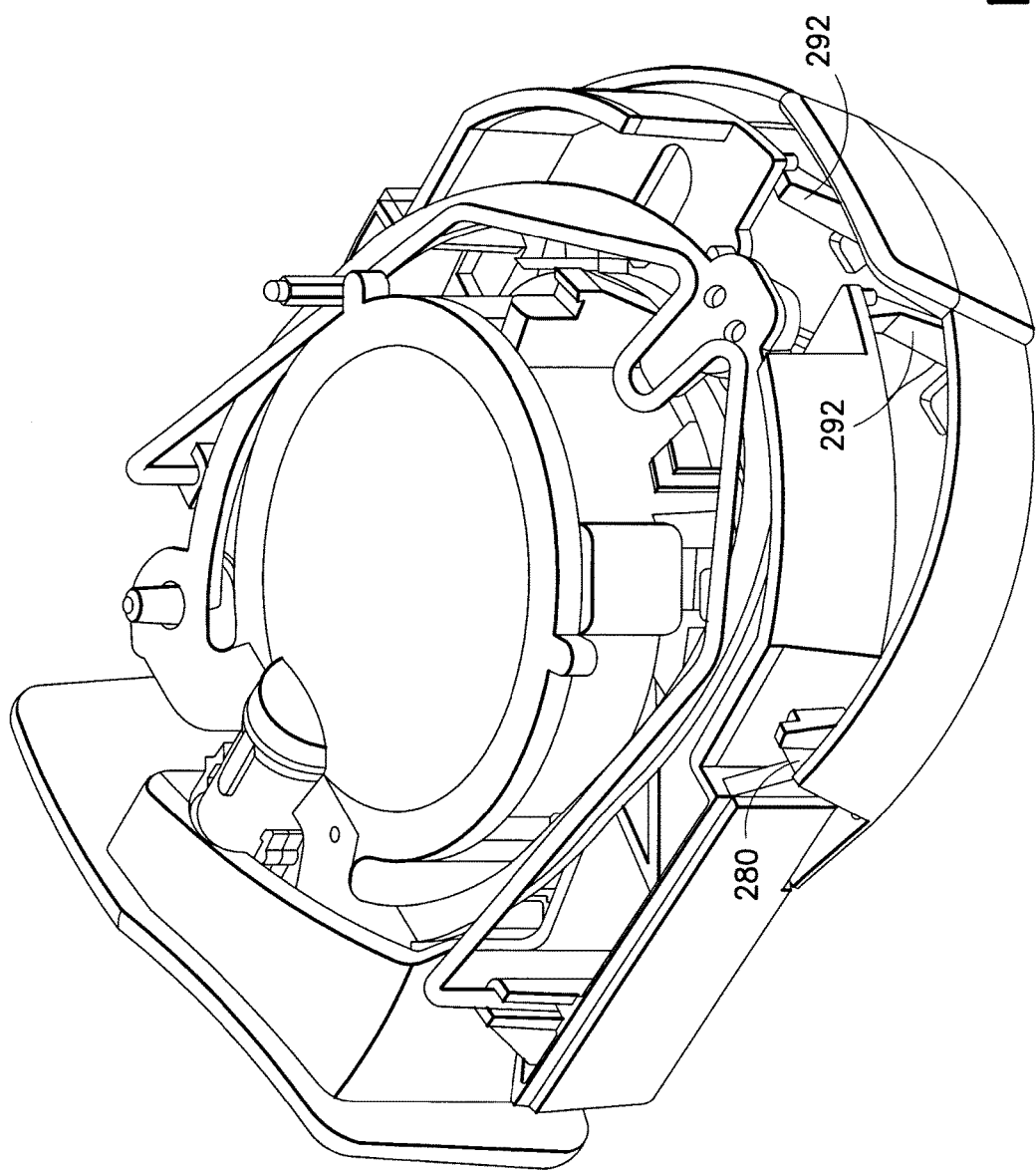
FIG. 11 illustrates a partially exploded view of the infusion device of FIG. 1 subsequent to deployment of the safety mechanism.
Figure 12:
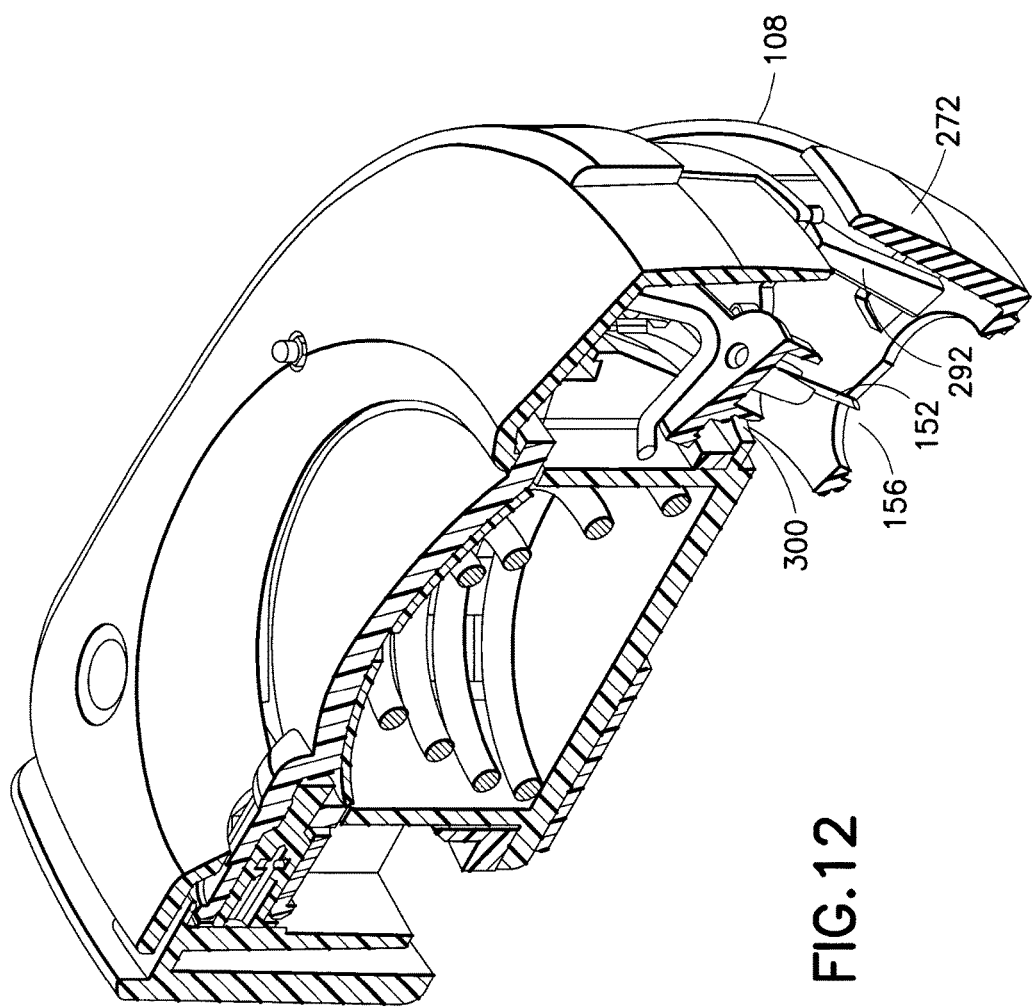
FIG. 12 illustrates a cross-sectional view of the infusion device of FIG. 1 subsequent to deployment of the safety mechanism.

In an embodiment of the device shown in FIGS. 1 through 12, a push-button design of the patch-like infusion device 100 is shown wherein the activation and energizing of the device is accomplished in a single multi-function/step process. FIG. 1 illustrates an assembled embodiment of the infusion device 100 in a pre-activated state. FIGS. 2-6 illustrate partially exploded and cross-sectional views of the infusion device 100 in the pre-activated state, FIG. 7 illustrates a partially exploded view of the infusion device 100 during installation of a safety mechanism, FIGS. 8-10 illustrate exploded and cross-sectional views of the infusion device 100 subsequent to activation, and FIGS. 11 and 12 illustrate exploded and cross-sectional views of the infusion device 100 subsequent to deployment of the safety mechanism. The infusion device 100 is configured to operate between the pre-activated state (shown, for example, in FIGS. 1, 2, and 5), an activated or fired state (shown, for example, in FIGS. 8-10), and a retracted or safe state (shown, for example, in FIGS. 11 and 12).

As shown in FIG. 1, an embodiment of the patch-like infusion device 100 includes a bottom enclosure 104, a safety mechanism 108, a flexible needle cover 112, a top enclosure 116, a reservoir subassembly 120, an end-of-dose indicator (EDI) 124, and an activator button 128, which includes a patient interface surface 132. Additionally, as shown in FIGS. 2-6, the infusion device 100 also includes a rotor or activation ring 136, a pressurization spring 140, a dome-like metal plunger 144, and a drive spring 148.

The flexible needle cover 112 provides patient and device safety by protecting at least one needle 152 (described in greater detail below) and providing a sterile barrier. The needle cover 112, protects the needle 152 during device manufacture, protects the patient prior to use, and provides a sterility barrier at any point prior to removal. According to one embodiment, the needle cover 112 is attached via a press fit with a needle manifold in which the at least one needle 152 is disposed. Additionally, according to one embodiment, a needle opening 156 (described in greater detail below) of the safety mechanism 108 is shaped to closely correspond to a perimeter of the needle cover 112.

As shown, for example, in FIGS. 2, 3, 5, 6, 8, 10, and 12, the reservoir subassembly 120 includes a reservoir 160, a reservoir dome seal 164, a valve 168, at least one needle 152, and at least one channel 172 (see, for example, FIG. 8) disposed between the valve 168 and the needle 152 and creating a flow path therebetween. The reservoir 160 includes a dome 176. Additionally, the reservoir subassembly 120 includes the removable needle cover 112 to selectively cover the at least one needle 152. According to one embodiment, the reservoir subassembly 120 also includes a reservoir arm seal 180, covering the channel 172. Preferably, the needle 152 includes a needle manifold and a plurality of microneedles 152.

The reservoir dome seal (flexible film) 164 of the reservoir subassembly 120, as shown, for example, in FIG. 5, is disposed between the plunger 144 and the dome 176. Reservoir contents (for example, medicinal material) for the infusion device 100 are disposed in the space between the reservoir dome seal 164 and the dome 176. The combination of the reservoir dome seal 164, the dome 176, and the space therebetween defines a reservoir 160. The dome 176 is preferably transparent to permit viewing of the reservoir contents. The reservoir dome seal 164 can be made of non-distensible materials or laminates, such as metal-coated films or other similar substances. For example, one possible flexible laminate film that can be used in the reservoir dome seal 164 includes a first polyethylene layer, a second chemical layer as known to those skilled in the art to provide an attachment mechanism for a third metal layer which is chosen based upon barrier characteristics, and a fourth layer that includes polyester and/or nylon. By utilizing a metal-coated or metallized film in conjunction with a rigid portion (for example, dome 176), the barrier properties of the reservoir 160 are improved, thereby increasing or improving the shelf life of the contents contained within. For example, where a reservoir content includes insulin, the primary materials of contact in the reservoir 160 include linear, low-density polyethylene (LLDPE), low-density polyethylene (LDPE), cyclic olefin copolymer (COC) and Teflon. As described in greater detail below, the primary materials of contact in the remaining flow path of the reservoir contents may also include COC and LLDPE, as well as thermoplastic elastomer (TPE), medical grade acrylic, stainless steel, and a needle adhesive (e.g. a UV cured adhesive). Such materials that remain in extended contact with the contents of the reservoir 160 preferably pass ISO 10-993 and other applicable biocompatibility testing.

The reservoir subassembly 120 is further preferably able to be stored for the prescribed shelf life of the reservoir contents in applicable controlled environments without adverse effect to the contents, and is capable of applications in a variety of environmental conditions. Additionally, the barrier provided by the components of the reservoir subassembly 120 do not permit the transport of gas, liquid, and/or solid materials into or out of the contents at a rate greater than that allowable to meet the desired shelf life. In the embodiments shown above, the reservoir materials are capable of being stored and operated in a temperature range of approximately 34 to 120 degrees Fahrenheit and can have a shelf life of two or more years.

In addition to satisfying stability requirements, the reservoir subassembly 120 can further ensure operation by successfully passing any number of leak tests, such as holding a 30 psi sample for 20 minutes without leaking. Additional filling, storage and delivery benefits resulting from the configuration of the reservoir include minimized headspace and adaptability as described in greater detail below.

In one embodiment, the reservoir 160 is evacuated prior to filling. By evacuating the reservoir 160 prior to filling and having only a slight depression in the dome 176, headspace and excess waste within the reservoir 160 can be minimized. In addition, the shape of the reservoir can be configured to adapt to the type of energizing mechanism (for example, pressurization spring 140 and plunger 144) used. Additionally, using an evacuated flexible reservoir 160 during filling minimizes any air or bubbles within the filled reservoir 160. The use of a flexible reservoir 160 is also very beneficial when the infusion device 100 is subjected to external pressure or temperature variations, which can lead to increased internal reservoir pressures. In such case, the flexible reservoir 160 expands and contracts with the reservoir contents, thereby preventing possible leaks due to expansion and contraction forces.

Yet another feature of the reservoir 160 includes the ability to permit automated particulate inspection at the time of filling, or by a patient at the time of use. One or more reservoir barriers, such as the dome 176, can be molded of a transparent, clear plastic material, which allows inspection of the substance contained within the reservoir. The transparent, clear plastic material is preferably a cyclic olefin copolymer that is characterized by high transparency and clarity, low extractables, and biocompatibility with the substance contained in the reservoir 160. A suitable material is available from Zeon Chemicals, L.P., of Louisville, Ky. under the designation "BD CCP Resin," and is listed by the U.S. Food and Drug Administration and DMF No. 16368. In such applications, the reservoir 160 includes minimal features that could possibly obstruct inspection (i.e. rotation during inspection is permitted).

Channel arm 172 is provided in the form of at least one flexible arcuate arm extending from the valve 168 to the needle manifold or microneedles 152. The arcuate arm has a groove 174 (see, for example, FIG. 2) formed therein. To provide a fluid path between valve 168 and the needle manifold or microneedles 152, the reservoir arm seal 180 covers the groove 174. The fluid path (disposed in channel arm 172—shown, for example, in FIG. 8) between the reservoir 160 and the microneedles 152 is constructed of materials similar or identical to those described above for the reservoir 160. For example, channel arm 172 may be constructed of the same material as the dome 160 and the reservoir arm seal 180 may constructed of the same material as the reservoir dome seal 164. According to one embodiment, both channel arms 172 are employed as fluid paths between the valve 168 and the needle manifold or microneedles 152. According to another embodiment, only one of the channel arms 172 is employed as a fluid path, and the remaining channel arm 172 provides structural support. In such an embodiment, the groove 174 extends fully from the valve 168 to the needle manifold or microneedles 152 only in the channel arm 174 that will be employed as the fluid path.

The channel arm 172 must be sufficiently flexible to withstand the force of activation. Contrasting the position of the channel arm 172 in FIGS. 2 and 8, the channel arm 172 (covered by reservoir arm seal 180 in FIG. 2, which is removed in FIG. 8 for clarity) elastically deforms when the microneedles 152 are driven into the patient's skin (described in greater detail below). During such deformation, the channel arm 172 must maintain the integrity of the fluid path between the valve 168 and the needle manifold or microneedles 152. Additionally, the materials for the channel arm 172 satisfy numerous biocompatibility and storage tests. For example, as shown in Table 1 below, where an infusion device content includes insulin, the primary materials of contact in the reservoir 160 include linear, low-density polyethylene, cyclic olefin copolymer, and Teflon, and can also include a transparent, clear plastic. The primary materials of contact in the remaining flow path (channel 62) between the reservoir 160 and the microneedles 152 of the needle manifold include COC and/or medical grade acrylic, LLDPE, TPE, and stainless steel, as well as the needle adhesive.

TABLE 1

| Path Component | Material |
| --- | --- |
| Reservoir | Polyethylene, cyclic olefin copolymer, and/or Teflon |
| Reservoir Dome Seal | Metal-coated film, such as polyethylene, aluminum, polyester, and/or nylon with a chemical tie layer |
| Valve | TPE |
| Needle Manifold | COC and/or medical grade acrylic |
| Needle adhesive | UV-cured adhesive |
| Microneedle | Stainless steel |

More specifically, the microneedles 152 can be constructed of stainless steel, and the needle manifold can be constructed of polyethylene and/or medical grade acrylic. Such materials, when in extended contact with the contents of the reservoir, preferably pass ISO 10-993 biocompatibility testing.

The valve 168, disposed between the reservoir 160 and the channel 172, selectively permits and restricts fluid flow between the reservoir 160 and the channel 172. The valve 168 moves between a pre-activated position (shown, for example, in FIGS. 2, 3, and 6) and an activated position (shown, for example, in FIGS. 8-10). When in the activated position, the valve permits fluid flow between the reservoir 160 and the channel 172, and therefore to the needle manifold and microneedles 152.

In use, the valve 168 will eventually be pushed into the activated position by the movement of the activator button 128, best illustrated by the movement of the valve 168 between FIGS. 5 and 10. As shown in FIG. 10, the movement of the valve 168 advances the enlarged distal end of the valve 168, thereby permitting the drug to flow from the reservoir 160 into the channel 172 and down the fluid path to the needle manifold.

The embodiment described above includes at least one needle 152, or microneedle 152, but may contain several, such as the two illustrated microneedles 152. Each microneedle 152 is preferably at least 31 gauge or smaller, such as 34 gauge, and is anchored within a patient needle manifold that can be placed in fluid communication with the reservoir 160. The microneedles 152, when more than one is included in the infusion device 100, can also be of differing lengths, or gauges, or a combination of both differing lengths and gauges, and can contain one or more ports along a body length, preferably located near the tip of the microneedle 152 or near the tip bevel if any of the microneedles 152 has one.

According to one embodiment, the gauge of the microneedles 152 governs the delivery rate of reservoir contents of the infusion device 100. The use of multiple 34 gauge microneedles 152 to deliver the reservoir contents is practical when the infusion occurs over a longer period than typically associated with an immediate syringe injection requiring a much larger cannula, or needle. In the disclosed embodiments, any microneedles 152 that target either an intradermal or subcutaneous space can be used, but the illustrated embodiments include intradermal microneedles 152 of between 1 and 7 mm in length (i.e., 4 mm). The arrangement of the microneedles 152 can be in a linear or nonlinear array, and can include any number of microneedles 152 as required by the specific application.

As noted above, the microneedles 152 are positioned in a needle manifold. In the needle manifold, at least one fluid communication path, or channel 172, is provided to each microneedle 152. The manifold may simply have a single path to one or more microneedles 152, or may provide multiple fluid paths or channels routing the reservoir contents to each microneedle 152 separately. These paths or channels may further comprise a tortuous path for the contents to travel, thereby affecting fluid pressures and rates of delivery, and acting as a flow restrictor. The channels or paths within the needle manifold can range in width, depth and configuration depending upon application, where channel widths are typically between about 0.015 and 0.04 inch, preferably 0.02 inch, and are constructed to minimize dead space within the manifold.

According to one embodiment, the reservoir subassembly 120 has a pair of holes 184 and 188 to aid registration of the reservoir subassembly 120 with respect to the bottom enclosure 104. First and second posts 192 and 196 (described in greater detail below) of the bottom enclosure 104 are inserted through the respective holes 184 and 188.

Figure 4:
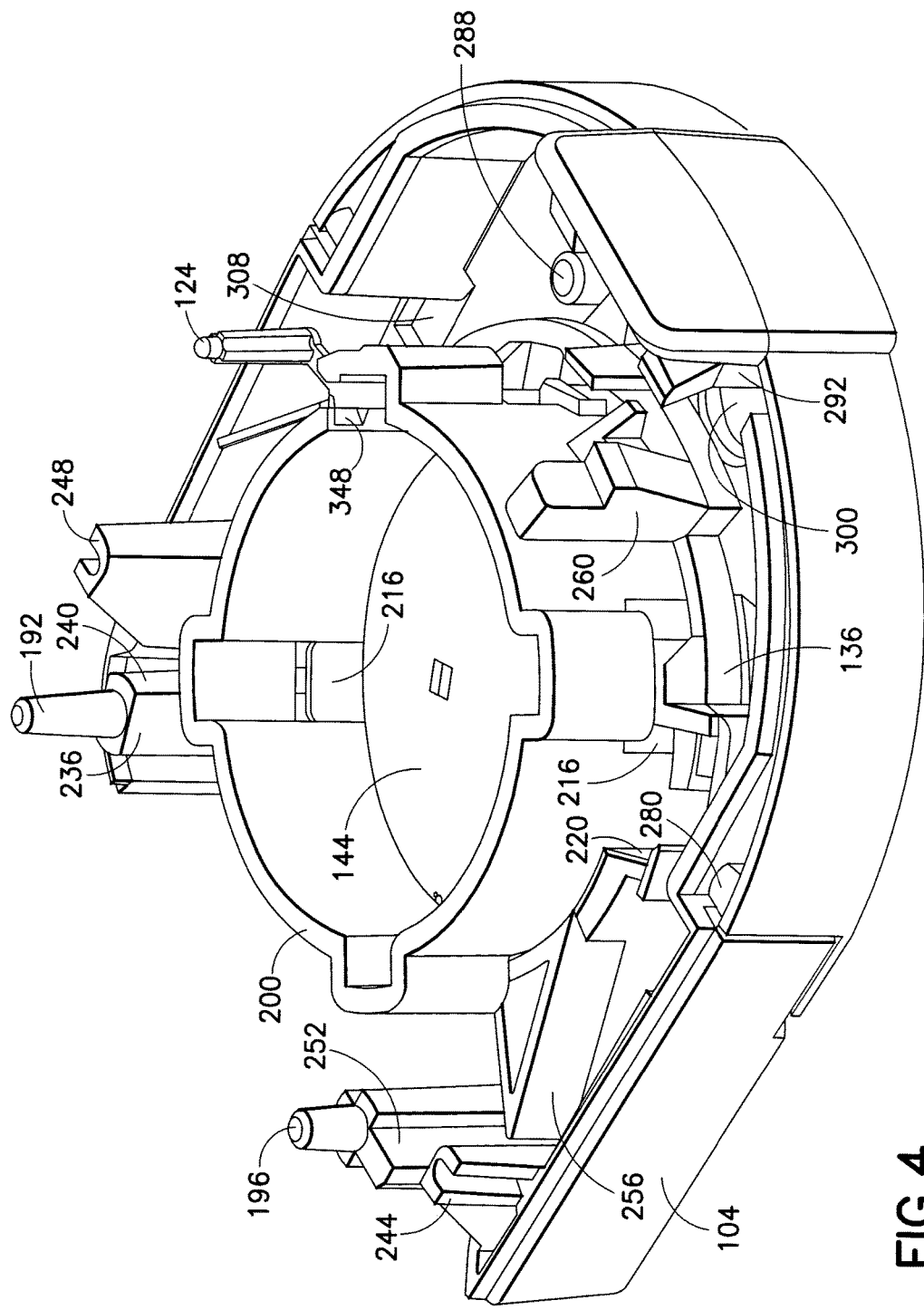
FIG. 4 illustrates a more fully exploded view of the infusion device of FIG. 1 in the pre-activated state.

In exploded views with the reservoir subassembly 120 removed, FIGS. 4, 7, and 9 illustrate that bottom enclosure 104 includes a substantially cylindrical housing 200 in which pressurization spring 140 and plunger 144 are disposed. According to one embodiment, cylindrical housing 200 includes a plurality of recessed channels 204 to guide a respective plurality of legs 208 and feet 212 of the plunger 144 as the plunger translates within the housing 200. Collectively, a leg 208 and a foot 212 constitute a plunger tab 214. As shown in FIGS. 4, 7, and 9, for example, the recessed channels 204 extend only part of the way down the cylindrical housing 200 from a top thereof. Below the recessed channels 204, there are openings 216 through which the feet 212 of plunger 144 can extend outside of the cylindrical housing 200. The openings 216 are substantially L-shaped with horizontal portions at the base of the cylindrical housing 200, and a vertical portion substantially aligned with the recessed channels 204.

When the infusion device 100 is in the pre-activated state, the pressurization spring 140 is compressed by the plunger 144 (as shown, for example, in FIGS. 4-6), and the feet 212 of the plunger 144 are substantially disposed in the horizontal portions of the openings 216. The force of the pressurization spring 140 biases the feet 212 of the plunger 144 against a top of the horizontal portions of the openings 216 (i.e., a ledge of the cylindrical housing 200). Together, as described in greater detail below, the pressurization spring 140 and the plunger 144 form a pressurization system to pressurize the reservoir 160 when the infusion device 100 is activated.

As described in greater detail below, the rotor 136 rotates around the base of the cylindrical housing 200 between a pre-activated position (illustrated, for example, in FIGS. 2-4) and an activated position (illustrated, for example, in FIGS. 8-10). When the rotor 136 rotates from the pre-activated position to the activated position, at least one foot engaging surface 220 (shown, for example, in FIG. 4) of the rotor 136 engages at least one of the feet 212 of the plunger 144 and rotates the plunger 144 so that the feet 212 align with the vertical portions of the openings 216 and the recessed channels 204. At this point, the pressurization spring 140 moves the plunger 144 upward with the feet 212 being guided by the raised channels 204.

The pressurization spring 140 is included in the infusion device 100 to apply an essentially even force to the reservoir 160, to force the contents from the reservoir 160. The pressurization spring 140 is used to store energy that, when released, pressurizes the reservoir 160 at the time of use. The pressurization spring 140 is held in a compressed state by engagement between feet 212 of the plunger 144 and the cylindrical housing 200. This engagement prevents the pressurization spring 140 from putting stress on a film (to be described later) of the reservoir 160 or any remaining device components (other than the bottom enclosure 104 and the plunger 144) during storage. The plunger 144 is sufficiently rigid to resist spring tension and deformation, and should not fail under normal load.

As noted above, when the rotor 136 rotates from the pre-activated position to the activated position, the rotor 136 engages at least one of the feet 212 of the plunger 144 and rotates the plunger 144 to align the feet 212 with the vertical portions of the openings 216 and the recessed channels 204. The compressed pressurization spring 140, then moves the plunger 144 upward, and in doing so, exerts a force on the film of the reservoir 160. The pressurization spring 140 can be configured to preferably create a pressure within the reservoir 116 of from about 1 to 50 psi, and more preferably from about 2 to about 25 psi for intradermal delivery of the reservoir contents. For sub-cutaneous injection or infusion, a range of about 2 to 5 psi may be sufficient.

According to one embodiment, the activator button 128 includes the patient interface surface 132 that the patient presses to activate the infusion device 100. The activator button 128 also includes a hinge arm 224 and an activation arm 228 (both shown, for example, in FIG. 3). The hinge arm 224 of the activator button 128 includes a cylindrical portion with an opening. The activation arm 228 includes a tab 230 (see, for example, FIG. 3). According to one embodiment, the tab 230 includes a bearing surface 232 and a locking surface 234 disposed adjacent to the cantilevered end of the bearing surface 232. According to one embodiment, the tab 230 forms an acute angle with a main portion of the activation arm 228.

The first post 192, disposed on the bottom enclosure 104, extends upwardly therefrom. According to one embodiment (as shown, for example, in FIGS. 4 and 7), a base of the first post 192 includes a pair of flat sides 236 and a pair of rounded sides 240. Additionally, as shown, for example, in FIGS. 4 and 7, the second post 196 and first and second drive spring bases 244 and 248 extend upwardly from the bottom enclosure 104. As will be described in greater detail below, the first and second drive spring bases 244 and 248 anchor respective ends of drive spring 148. The first drive spring base 244 is disposed adjacent to the second post 196 with a space therebetween.

Figure 3:
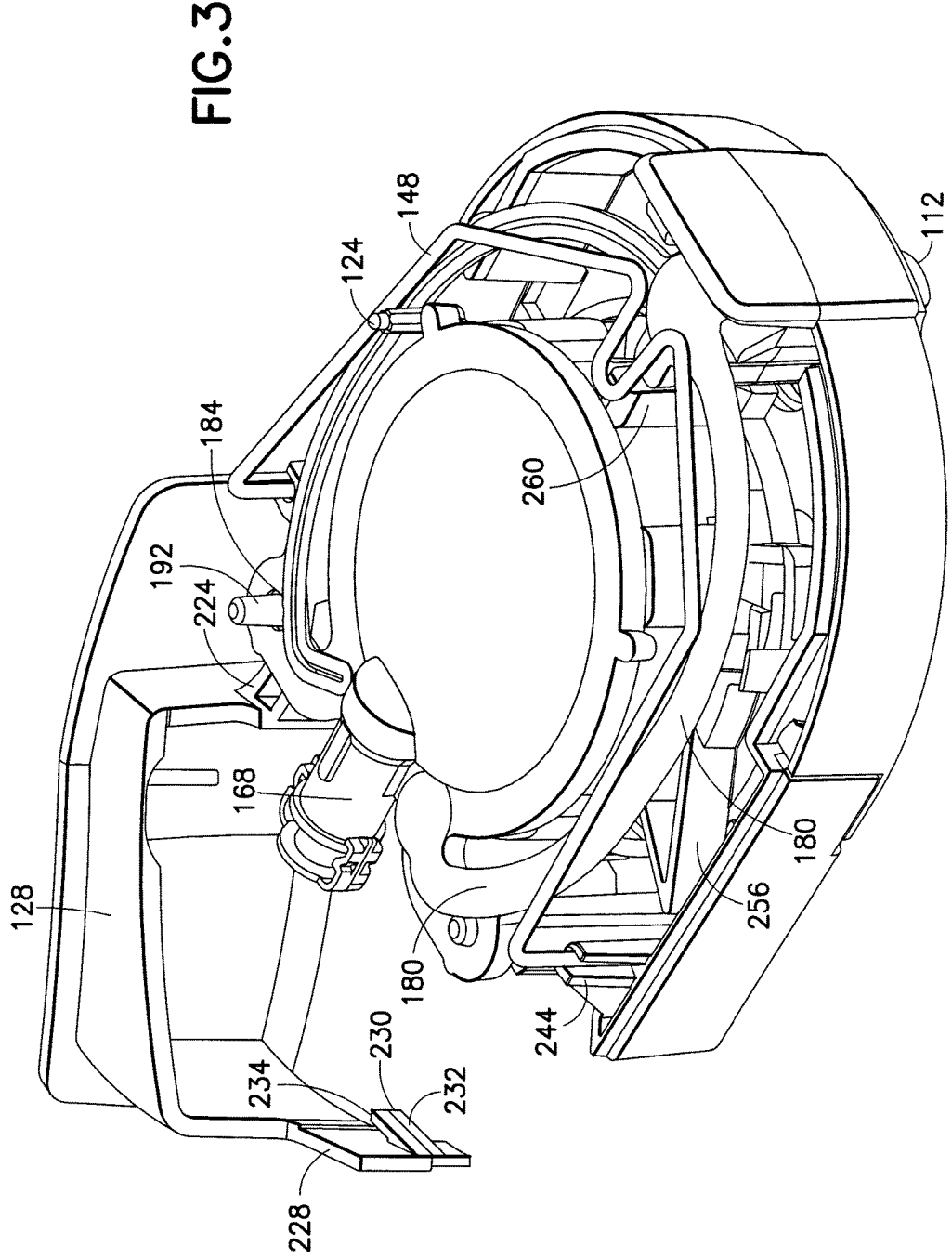
FIG. 3 illustrates a partially exploded view of the infusion device of FIG. 1 in the pre-activated state with an activator button rotated away to reveal more detail.

According to one embodiment, FIGS. 3 and 6 illustrate the positioning of the activator button 128 with respect to the bottom enclosure 104, for assembly of the activator button 128. In this position, the opening of the cylindrical portion of the hinge arm 224 allows the activator button 128 to slide horizontally (passing the flat sides 236) and engage the first post 192. The hinge arm 224 (and therefore the activator button 128) can then rotate about the first post 192. As the activation arm 228 passes into the space between the second post 196 and the first drive spring base 244, at least one of the tab 230 and the activation arm 228 elastically deforms until a cantilevered end of the bearing surface 232 of tab 230 passes a retaining face 252 of the second post 196. The passage of the cantilevered end of the bearing surface 232 of tab 230 past the retaining face 252 (see, for example, FIG. 4) of the second post 196 and the engagement of the locking surface 234 of tab 230 with the retaining face 252 provides an audible click and tactile feedback conveying that the activator button 128 is in the pre-activated position.

Referring back to FIGS. 2-4, and 7-9, rotor 136 additionally includes an activation projection 256 and a drive spring holder 260. The activation arm 228 of the activator button 128 engages the activation projection 256 when a patient depresses the activator button 128, thereby rotating the rotor 136 from the pre-activated position to the activated position.

The drive spring holder 260 maintains the drive spring 148 in a pre-activated position when the rotor 136 is in the pre-activated position. As noted previously, the first and second drive spring bases 244 and 248 anchor opposing ends of the drive spring 148. At approximately a midpoint of the drive spring 148, there is a substantially U-shaped projection as shown, for example, in FIGS. 2 and 3, for engagement with the drive spring holder 260 of the rotor 136. Accordingly, when the rotor 136 is in the pre-activated position and the drive spring 148 engages the drive spring holder 260, the drive spring 148 is maintained in a tensile state. And when the drive spring holder 260 releases the drive spring 148 (i.e., when the rotor rotates from the pre-activated position to the activated position as illustrated, for example, in FIGS. 8-10), the drive spring 148 drives the microneedles 152 to extend outside of the infusion device 100 through an opening 300 in the bottom enclosure 104 (and through an opening in the safety mechanism 108 described in greater detail below).

Thus, as will be described in greater detail below, the activation and energizing of the infusion device 100 that is accomplished in a single multi-function/step process includes depression of the activator button 128 by a patient, and rotation of the rotor 136 due to engagement between the activation arm 228 of the activator button 128 and the activation projection 256 of the rotor 136. As described above, the rotation of the rotor 136 rotates and releases the plunger 144 to pressurize the fluid within the reservoir 160. Additionally, the rotation of the rotor 136 releases the drive spring 148 from the drive spring holder 260, thereby driving the microneedles 152 to extend outside of the infusion device 100. The single multi-function/step process also includes movement of the valve 168 from the pre-activated position to the activated position due to the activator button 128 engaging and moving the valve 168 when the activator button 128 is depressed, thereby commencing fluid flow between the reservoir and the microneedles 152 via the channel 172.

As noted above, the patch-like infusion device 100 also includes a safety mechanism 108. To prevent inadvertent or accidental needle stick injuries, prevent intentional re-use of the device, and to shield exposed needles, the locking needle safety mechanism 108 is provided. The safety mechanism 108 automatically activates immediately upon removal of the infusion device 100 from the skin surface of the patient. According to one embodiment described in greater detail below, a flexible adhesive pad 264 adheres to a bottom portion of the bottom enclosure 104 and a bottom portion of the safety mechanism 108. The adhesive pad 264 contacts with the patient's skin and holds the infusion device 100 in position on the skin surface during use. As shown, for example, in FIGS. 11 and 12, upon removal of the infusion device 100 from the skin surface, the safety mechanism 108 extends to a position shielding the microneedles 152. When fully extended, safety mechanism 108 locks into place and prevents accidental injury or exposure to the patient needles 152.

In general, a passive safety system is most desirable. This allows the device to be self-protecting in case of accidental removal or if the patient forgets that there is a safety step. Because one typical use for this infusion device 100 is to provide human growth hormone, which is usually given in the evening, it can be expected that patients that wear the device (such as children) may actually wear them overnight, even though the delivery may be expected to take less than 10 minutes. Without a passive system, if the infusion device 100 falls off, the microneedles 152 could re-stick the patient or a caregiver. The solution is to either limit the activities during use, or include a passive safety system.

With respect to safety systems, there are typically three options. A first option is to retract the needles 152 into the device. A second option is to shield the needles 152 to remove access, and a third option is to destroy the needles 152 in a way that prevents needle stick injuries. Other systems, such as active systems, utilize manual shielding and/or destruction, or manual release of safety features with an additional button push or similar action. A detailed description of passive safety embodiments of the present invention is described below.

One safety embodiment of the present invention is a passive, fully enclosed pull-out design embodiment, such as safety mechanism 108. FIGS. 5, 10, and 12 are perspective cutaway views of the infusion device 100 that illustrate the safety mechanism 108 prior to activation, subsequent to activation, and subsequent to deployment of the safety mechanism 108, respectively.

Figure 13:
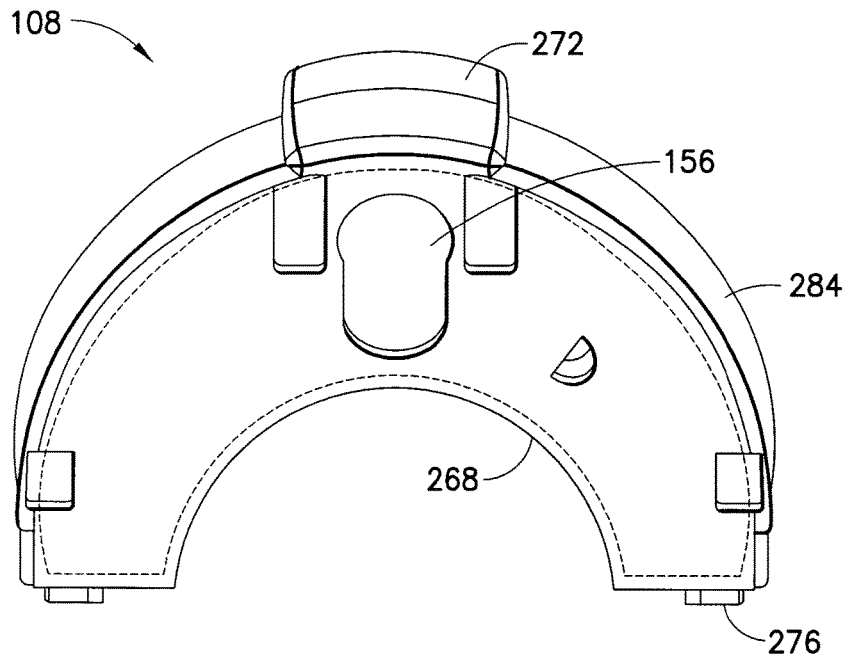
FIG. 13 illustrates a bottom surface of the safety mechanism.

When the infusion device 100 is removed from the skin, the flexible adhesive pad 264 (attached to both the bottom surface of the bottom enclosure 104 and the bottom surface of the safety mechanism 108) will pull the safety mechanism 108 out and lock it into place before the adhesive pad 264 releases the skin surface. In other words, the force required to remove the adhesive pad from the skin surface is greater than that required to deploy the safety mechanism 108. According to one embodiment, the safety mechanism 108, as shown, for example, in FIG. 13, includes a flat surface portion 268 that is in contact with the patient's skin. The flat surface 268 is where a portion of adhesive pad 264 (shown as a dotted line in FIG. 13) is affixed to safety mechanism 108 such that when the infusion device 100 is removed by the patient from the skin, the adhesive pad 264 will act to deploy the safety mechanism 108 from the infusion device 100, thereby shielding the microneedles 152, which otherwise would be exposed upon removal of the infusion device 100 from the patient. When the safety mechanism 108 is fully extended, the safety mechanism 108 locks into place and prevents accidental injury or exposure to the microneedles 152.

According to one embodiment, the adhesive pad 264 is provided in substantially two parts, one on the bulk of the bottom surface of the bottom enclosure 104, and one on the bottom surface of the safety mechanism 108. When the infusion device 100 is removed, the two patches move independently and the safety mechanism 108 is rotatable with respect to the bottom enclosure 104. According to another embodiment, the two parts are formed as a unitary, flexible adhesive pad 264 with one part being disposed on the on the bulk of the bottom surface of the bottom enclosure 104, and one part disposed on the bottom surface of the safety mechanism 108.

Figure 14:
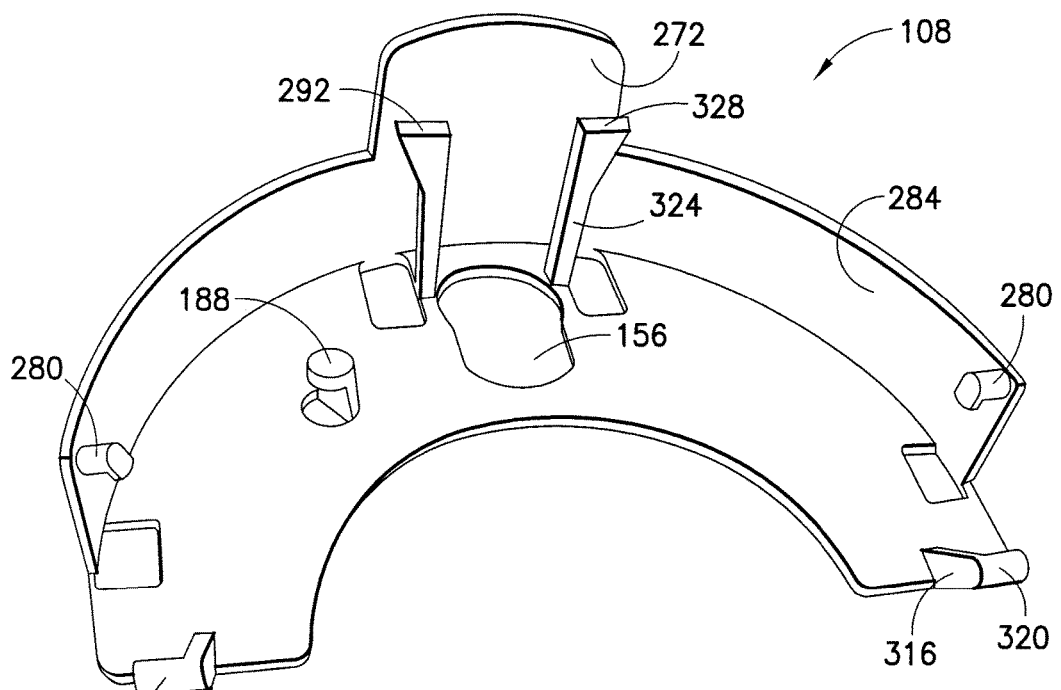
FIG. 14 further illustrates the structure of the safety mechanism.

According to one embodiment, the safety mechanism 108 is a stamped metal part. According to another embodiment, the safety mechanism 108 is made of substantially the same material as the bottom enclosure 104. As shown in FIG. 14, the safety mechanism 108 includes a front shield 272, a pair of insertion tabs 276 disposed at a rear portion of the safety mechanism 108, a pair of pivot tabs 280 disposed, respectively, at upper rear ends of a rim portion 284 of the safety mechanism 108, a guide post 288 extending upwardly from a substantially flat bottom inner surface of the safety mechanism 108, and locking posts 292 also extending upwardly from the bottom inner surface of the safety mechanism 108. Front shield 272 extends above the rim portion 284 to shield the patient from the microneedles 152 when the safety mechanism 108 is deployed. The guide post 288 includes a cutout therein to engage a safety retaining projection 296 of the rotor 136 (shown, for example, in FIGS. 7 and 9) when the rotor 136 is in the pre-activated position, to prevent the safety mechanism 108 from deploying prior to activation of the infusion device 100.

Additionally, as noted above, the safety mechanism 108 includes the needle opening 156. Prior to deployment of the safety mechanism 108, the needle opening 156 at least partially overlaps the opening 300 in bottom enclosure 104 to provide space for movement of the microneedles 152. The locking posts 292 are respectively disposed adjacent to front side edges of the needle opening 156. The bottom enclosure 104 includes a guidepost opening 304 (shown, for example, in FIGS. 7 and 9), a pair of insertion tab openings 308 (one of which is shown, for example, in FIG. 4) disposed adjacent to opposing side edges of the bottom enclosure 104, and a pair of pivot rests 312 disposed on opposing sides of the bottom enclosure 104 (shown, for example, in FIGS. 7 and 9).

Referring again to FIG. 14, insertion tabs 276 each include a connecting portion 316 and an extending portion 320. According to one embodiment, the connecting portions 316 extend from the bottom inner surface of the safety mechanism 108 toward a rear of the infusion device 100 at a non-perpendicular angle with respect to the bottom inner surface of the safety mechanism 108. Extending portions 320 each extend substantially perpendicularly from the extending portions 320 toward respective outer sides of the safety mechanism 108. To assemble the safety mechanism 108 to the bottom enclosure 104, safety mechanism 108 is held at an approximately 45° angle with respect to the bottom enclosure 104 and the insertion tabs 276 are inserted through the insertion tab openings 308. The safety mechanism 108 is then rotated to a position such that the guidepost 288 is inserted through the guidepost opening 304 and the bottom inner surface of the safety mechanism 108 is substantially parallel and in contact with the bottom surface of the bottom enclosure 104.

Referring again to FIGS. 7 and 9, although these views illustrate the rotor 136 in the activated position, the exploded nature of FIGS. 7 and 9 is convenient to illustrate this stage of the assembly of the safety mechanism 108 to the bottom enclosure 104. It will be understood, however, that the safety mechanism 108 should be assembled to the bottom enclosure prior to activation. Subsequent to the upward rotation of the safety mechanism 108, as shown in FIG. 4, safety mechanism 108 translates rearward with respect to the bottom enclosure 104 such that pivot tabs 280 clear respective front edges of the pivot rests 312 and are disposed above the pivot rests 312, the locking posts 292 are disposed adjacent to side edges of the opening 300 of the bottom enclosure 104, and the safety retaining projection 296 of the rotor 136 engages the guide post 288.

Returning to FIG. 14, each of the locking posts 292 includes a post extending portion 324 extending substantially perpendicular from the flat bottom inner surface of the safety mechanism 108, and a wedge portion 328 disposed at an end of the post extending portion 324. As a height of the wedge portion 328 increases with respect to the bottom inner surface of the safety mechanism 108, a width of the wedge portion 328 increases.

As the safety mechanism 108 deploys and rotates downward with respect to the bottom enclosure 104, the wedge portions 328 act against respective side edges of the openings 180 of the bottom enclosure 104, causing the locking posts 192 to deform elastically toward one another. As the safety mechanism 108 is fully deployed, the tabs 280 become seated in pivot rests 312. Additionally, top edges of the wedge portions 328 pass bottom edges of the opening 300 and the locking posts 292 snap back to their substantially un-deformed states, providing an audible click and tactile feedback communicating that the safety mechanism 108 is fully deployed, and therefore, that the microneedles 152 are covered. Returning to FIGS. 11 and 12, once the safety mechanism 108 is fully deployed and the locking posts 292 have snapped back to their substantially un-deformed states, the top edges of the wedge portions 328 engage the bottom surface of the bottom enclosure 104 adjacent to the opening 300, thereby preventing the safety mechanism 108 from rotating upward with respect to the bottom enclosure 104 and exposing the microneedles 152. Additionally, as noted above, front shield 272 shields the patient from the microneedles 152.

Accordingly, the safety mechanism 108 is a passive safety embodiment provided as a single part and provides a good lock that will not crush under human loads. With this passive safety mechanism, no additional forces are applied to the skin during injection, and the microneedles 152 are safely held within the infusion device 100 after use.

After use of the infusion device 100, the patient can once again inspect the device to ensure the entire dose was delivered. In this regard, according to one embodiment as shown in FIGS. 15A-D, the infusion device 100 includes the end-of-dose indicator (EDI) 124. The EDI 124 includes a main body or post 332 and first and second arms 336 and 340 extending substantially horizontally with respect to a top of the main body 332.

The EDI 124 also includes a spring arm 344 that curves upwardly from the top of the main body 332. According to one embodiment, the spring arm 344 pushes against a bottom side of the reservoir subassembly 120, elastically biasing the EDI 124 toward the bottom enclosure 104, to ensure that the EDI 124 does not move freely out of the infusion device 100, for example, during shipping and handling of the infusion device 100. According to one embodiment, the spring arm 344 pushes against a bottom side of the dome 176.

Returning to FIG. 4, the main body 332 is disposed in an EDI channel 348 and translates substantially vertically therein. According to one embodiment, the EDI channel is disposed adjacent to one of the recessed channels 204 that guides legs 208 and feet 212 of plunger 144. The first arm 336 extends across a top of this recessed channel 204.

Returning to FIG. 15A, a vertical extrusion or signaling post 352 extends upwardly from an end of the second arm 340. When the reservoir contents have been delivered, the signaling post 352 extends through an EDI opening 356 (see, for example, FIG. 15C) in the top enclosure 116 to communicate that the end of the dose has been reached. According to one embodiment, the EDI 124 is formed as a one-piece construction.

As shown in FIG. 15B, as the plunger 144 travels upwardly in the cylindrical housing 200 due to the pressurization spring 140 subsequent to activation, one of the feet 212 of the plunger 144 contacts the first arm 336 of the EDI 124. The foot 212 lifts the EDI 124 upward, overcoming the bias of the spring arm 344, and causing the signaling post 352 to increasingly extend through the EDI opening 356 during delivery of the reservoir contents. Referring back to FIG. 10, as the medicament is being expelled from the reservoir 160 subsequent to activation, the signaling post 352 partially extends from the infusion device 100. Once the delivery of the reservoir contents is complete and the plunger has achieved its full stroke, the vertical extrusion 352 is fully extended, as shown in FIG. 15D. Thus, the EDI 124 employs the linear movement of the plunger 144 to generate linear movement of the EDI 124 that is visible outside the infusion device 100, thereby communicating the delivery of the reservoir contents.

FIGS. 16A and 16B illustrate another end-of-dose indicator (EDI) 360 and the operation thereof in the infusion device 100. As shown in FIG. 16A, a base 364 of a signaling post 368 of the EDI 360 is a different color than the remainder of the signaling post 368. As shown in FIG. 16B, visibility of the base 364 outside the infusion device 100 signals that delivery of the medicament is substantially complete. In other respects, the EDI 360 is substantially similar to the EDI 124.

FIGS. 17A and 17B illustrate yet another end-of-dose indicator (EDI) 372. As shown in FIGS. 17A and 17B, the EDI 372 includes a main body 376, a first arm 380 extending from the main body 376, and first and second spring arms 384 and 388 also extending from the main body 376. Additionally, a signaling post 392 extends from an end of the first arm 380. According to one embodiment, the signaling post 392 includes a base 396 and a top 400. According to one embodiment, at least a portion of the base 396 is a different color than the remainder of the signaling post 392. In such an embodiment, visibility of the different-colored portion of the base 396 outside the infusion device 100 signals that delivery of the medicament is substantially complete.

Figure 18:
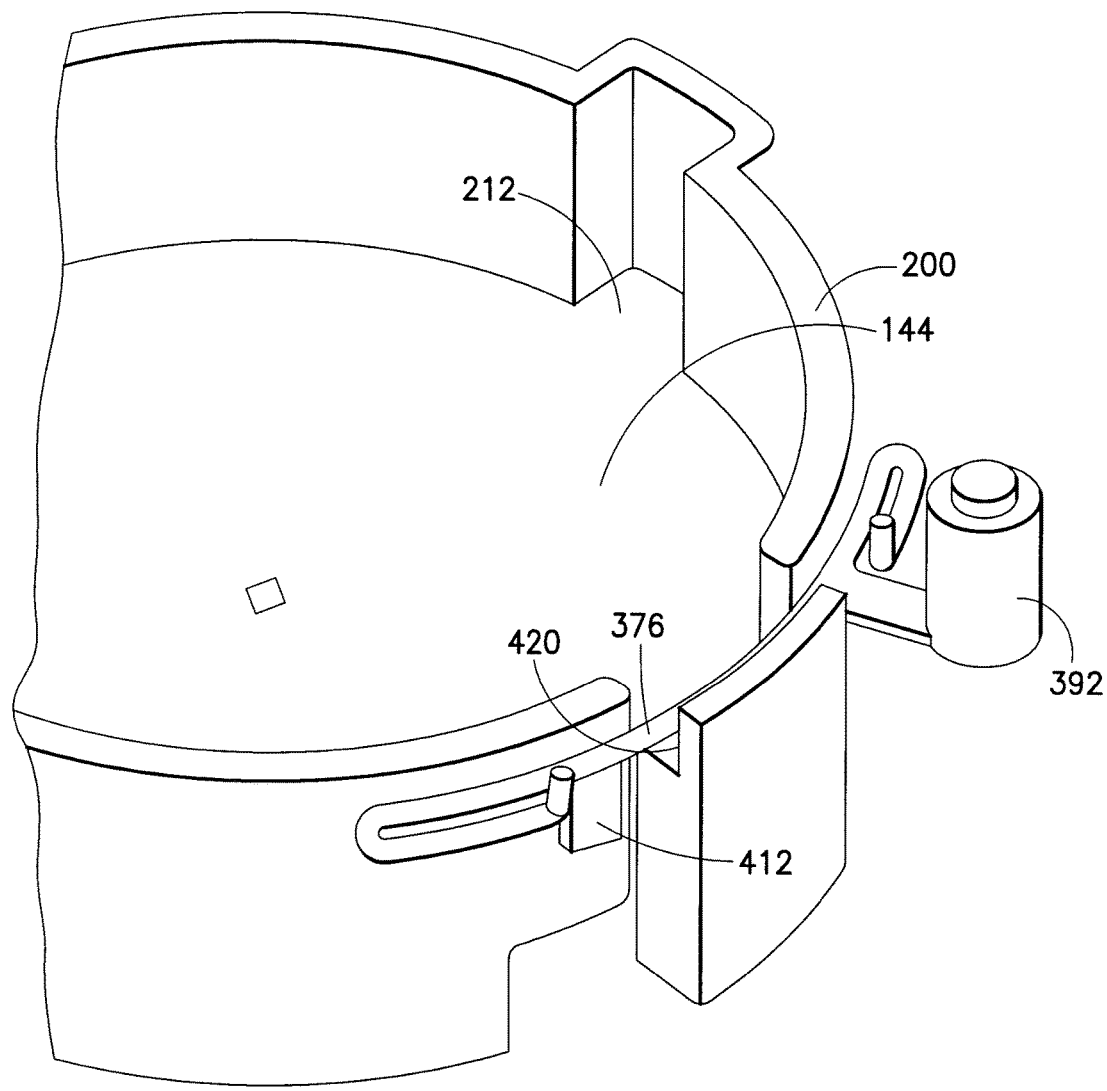
FIG. 18 illustrates the end-of-dose indicator of FIG. 17A disposed in the infusion device of FIG. 1.

As shown in FIG. 17A, the EDI 372 also includes a pair of stabilizing arms 412 and 416 extending from the main body 376. The stabilizing arms 412 and 416 stabilize the EDI 372 during the movement thereof. FIG. 18 illustrates the EDI 372 disposed in the infusion device. As shown in FIG. 18, the cylindrical housing 200 includes a channel 420 movably housing the main body 376 of the EDI 372. The stabilizing arms 412 and 416 contact an outside of the cylindrical housing 200 to stabilize the EDI 372 during the movement thereof.

Subsequent to activation, as the plunger 144 travels within the cylindrical housing 200, a foot 212 of the plunger 144 contacts and lifts the main body 376 of the EDI 372, thereby converting a motion of the plunger 144 into motion of the main body 376, and thus motion of the signaling post 392.

The first and second spring arms 384 and 388 each have a spring arm post 404, 408 disposed at respective ends thereof. According to one embodiment, the spring arm posts 404 and 408 contact a bottom side of the reservoir subassembly 120, elastically biasing the EDI 372 inwardly with respect to the top enclosure 116 in combination with the spring arms 384 and 388, to ensure that the EDI 372 does not extend out of the infusion device 100 prior to the end of the dosage, for example, during shipping and handling of the infusion device 100. According to one embodiment, the spring arm posts 404 and 408 push against a bottom side of the dome 176.

As the plunger 144 reaches the end of its travel stroke, the force of the pressurization spring 140 on the plunger 144 overcomes the bias of the first and second spring arms 384 and 388, inducing the signaling post 392 to extend outside the infusion device 100 and thereby signal that delivery of the medicament is substantially complete.

FIGS. 19A and 19B respectively illustrate still another end-of-dose indicator (EDI) 424 and the operation thereof. As shown in FIG. 19A, the EDI 424 includes a post 428 having a helical face 432. The EDI 424 also includes an arm 436 extending from an end of the post 428, and a vertical extrusion or signaling post 440 extending from an end of the arm 436 through an EDI opening 444 (see FIG. 20A) in the top enclosure 116 to be visible from outside the infusion device 100. According to one embodiment, the EDI opening 444 is an arcuate slot. The post 428 also has base 448 for rotatably connecting the EDI 424 to the bottom enclosure 104.

FIG. 19B illustrates the helical face 432 contacting a side edge of the plunger 144. FIG. 20A illustrates the infusion device 100 in a pre-activated state. According to one embodiment, the helical face 432 of the EDI 424 bears against the edge of the plunger 144 throughout the motion of the plunger. Thus, as the plunger 144 travels upwardly within the cylindrical housing 200 subsequent to activation, the contact between the edge of the plunger 144 and the helical face 432 causes the EDI 424 to rotate. According to one embodiment, the interaction between the helical face 432 and the edge of the plunger 144 during motion of the plunger 144 induces less than a full rotation of the post 428. In other words, the pitch of the helical face 432 induces less than a full rotation of the post 428 during the motion of the plunger 144.

As the EDI 424 rotates, the signaling post 440 correspondingly rotates within the EDI opening 444. And as the signaling post 440 reaches the end of the EDI opening 444, as shown in FIG. 20B, the EDI 424 indicates that delivery of the medicament is substantially complete.

Similar to FIGS. 19A and 19B, FIGS. 21A and 21B illustrate still another end-of-dose indicator (EDI) 452 and the operation thereof. As shown in FIG. 21A, the EDI 452 includes a post 456 having a helical face 460. In addition, the post 428 has a base 462 for rotatably connecting the EDI 452 to the bottom enclosure 104. The EDI 452 also includes a signaling indicator 464 on a top thereof, the signaling indicator 464 being visible from outside the infusion device 100 through an EDI opening 468 (see FIG. 22A) in the top enclosure 116.

FIG. 21B illustrates the helical face 460 contacting a side edge of the plunger 144. FIG. 22A illustrates the infusion device 100 in a pre-activated state. According to one embodiment, the helical face 432 of the EDI 424 bears against the edge of the plunger 144 throughout the motion of the plunger. Accordingly, as the plunger 144 travels upwardly within the cylindrical housing 200 subsequent to activation, the contact between the edge of the plunger 144 and the helical face 460 causes the EDI 424 to rotate. In comparison to the EDI 424 of FIG. 19A, the helical face 460 has a finer pitch. Thus, the EDI 452 rotates more during the stroke of the plunger 144 and the EDI 424. According to one embodiment, the interaction between the helical face 460 and the edge of the plunger 144 during motion of the plunger 144 induces at least one full rotation of the post 456. In other words, the pitch of the helical face 460 induces at least one full rotation of the post 456 during the motion of the plunger 144. According to one embodiment, the EDI 452 rotates more than one full rotation during the stroke of the plunger 144.

According to one embodiment, the signaling indicator 464 is, for example, an arrow. Correspondingly, on exterior portion of the top enclosure 116 adjacent to the EDI opening 468, there is at least one marker 472. As the EDI 452 rotates within the EDI opening 468 due to the stroke of the plunger 144, the rotation of the signaling indicator 464 with respect to the marker 472 is visible from outside the infusion device 100 thereby indicating a progress of the delivery of the medicament.

According to one embodiment, the pitch of the helical face 460 is defined to induce just less than two full rotations of the post 456 during the stroke of the plunger 144. Accordingly, as shown in FIG. 22B, after traveling just less than 2 full rotations, the EDI 452 indicates that delivery of the medicament is substantially complete.

Figure 23A:
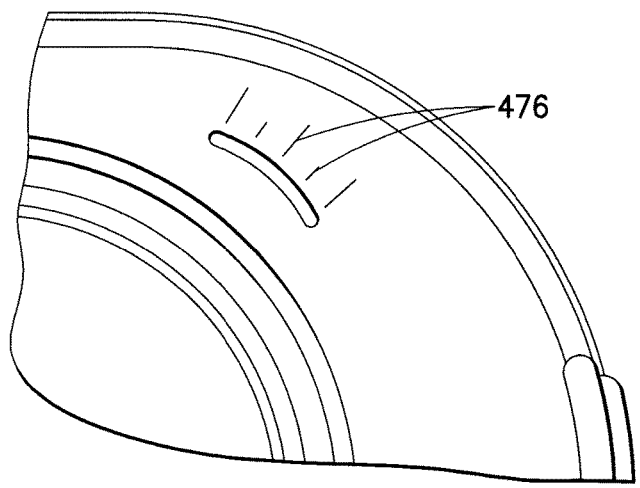
FIGS. 23A-23C illustrate embodiments of markers for indicating progress of delivery of a medicament.
Figure 23B:
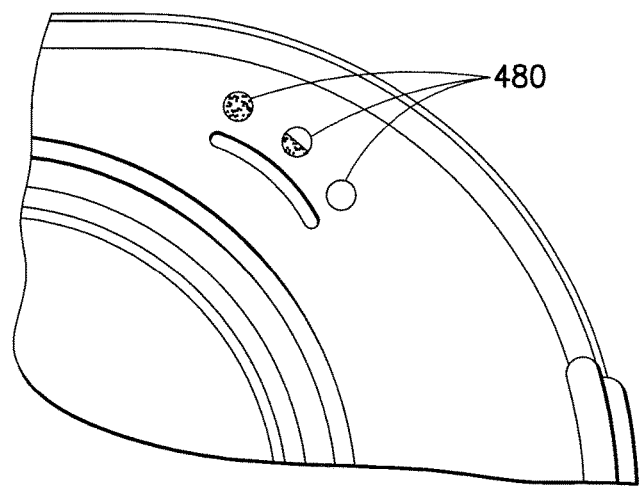
Figure 23C:
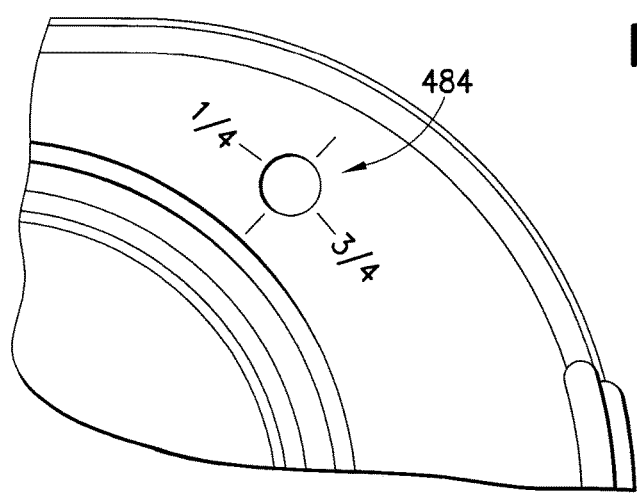

As shown in FIGS. 23A-23C, various markers may be employed adjacent an EDI opening on the top enclosure 116 to indicate progress of delivery of the medicament. For example, FIG. 23A illustrates a marker 476 that includes a scale with gradations. Such a marker 476 paired with an arcuate EDI opening can be employed with EDI 424. It will be generally understood however, that various markers may also be employed with variously-shaped EDI openings and various EDI embodiments.

FIG. 23B illustrates a marker 480 that includes icons denoting the state of fullness of the reservoir 160. For example, one icon indicates that the reservoir 160 is substantially full, a middle icon indicates that the reservoir 160 is substantially half-full, and therefore that delivery of the medicament is substantially half complete, and a third icon indicates that the reservoir 160 is substantially empty, and therefore that delivery of the medicament is substantially complete.

FIG. 23C illustrates a marker 484 that includes fraction icons denoting the state of fullness of the reservoir 160 or the fraction of medicament delivery that is complete, depending upon the direction of rotation of the corresponding EDI. For example, if a clockwise-rotating EDI with an arrow signaling indicator were employed with the marker 484, the motion of such an EDI would indicate the state of fullness of the reservoir 160. In contrast, if a counterclockwise-rotating EDI with an arrow signaling indicator were employed with the marker 484, the motion of such an EDI would indicate the fraction of medicament delivery that has been completed.

Figure 24A:
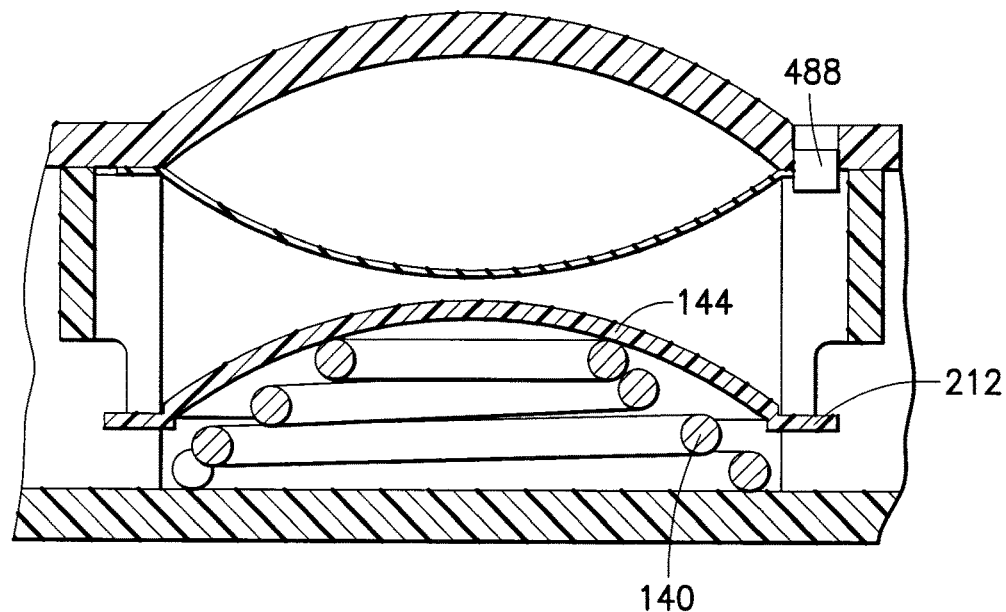
FIGS. 24A and 24B illustrate a further end-of-dose indicator and the operation thereof.
Figure 24B:
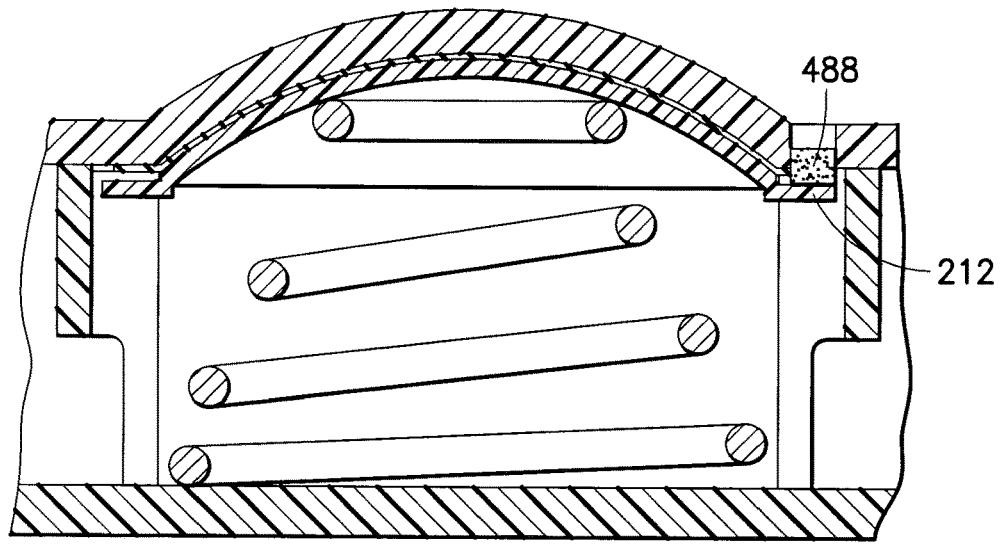

FIGS. 24A and 24B illustrate a further end-of-dose indicator (EDI) 488 and the operation thereof. According to one embodiment, the EDI 488 is a pressure-sensitive strip 488. When the plunger 144 reaches the end of its travel stroke, pressure of the plunger 144 (due to the force of the pressurization spring 140) is imparted to the pressure-sensitive strip 488. The pressure against the pressure-sensitive strip 488 induces a color change, thereby indicating that delivery of the medicament is substantially complete. The color change is visible because the top of the reservoir (for example, a window therein) is transparent.

According to one embodiment, the EDI 488 is disposed within the reservoir 160, for example, on an interior surface of the transparent dome 176. At the end of the travel stroke of the plunger 144, the pressure of the plunger 144 against the reservoir dome seal 164 is transferred by the reservoir dome seal 164 to the pressure-sensitive strip 488, inducing the color change thereof.

Figure 25A:
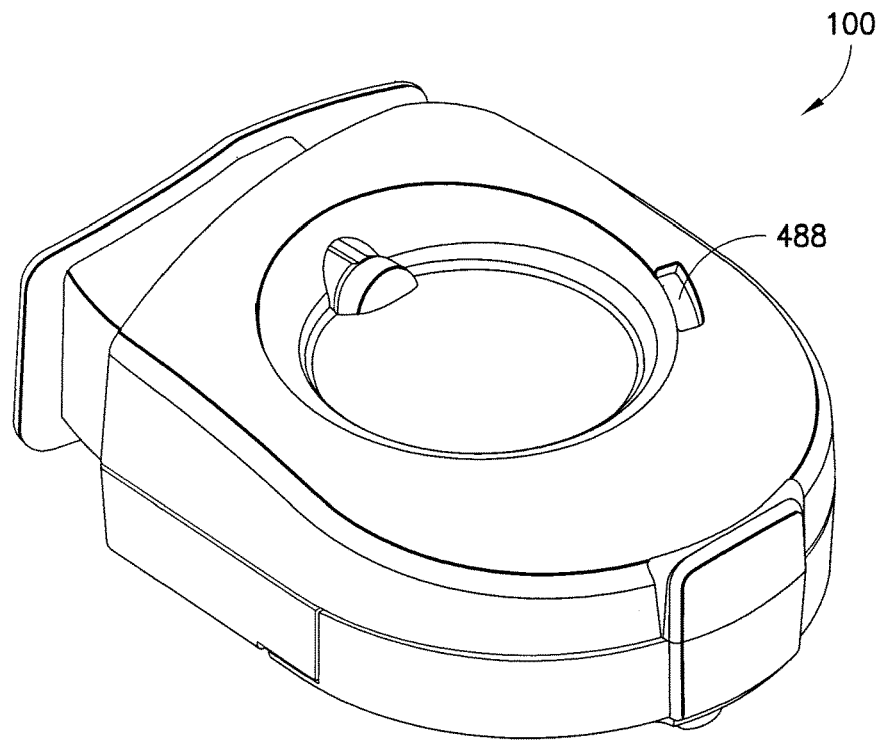
FIGS. 25A and 25B indicate the operation of the end-of-dose indicator of FIG. 24A in the infusion device of FIG. 1.
Figure 25B:
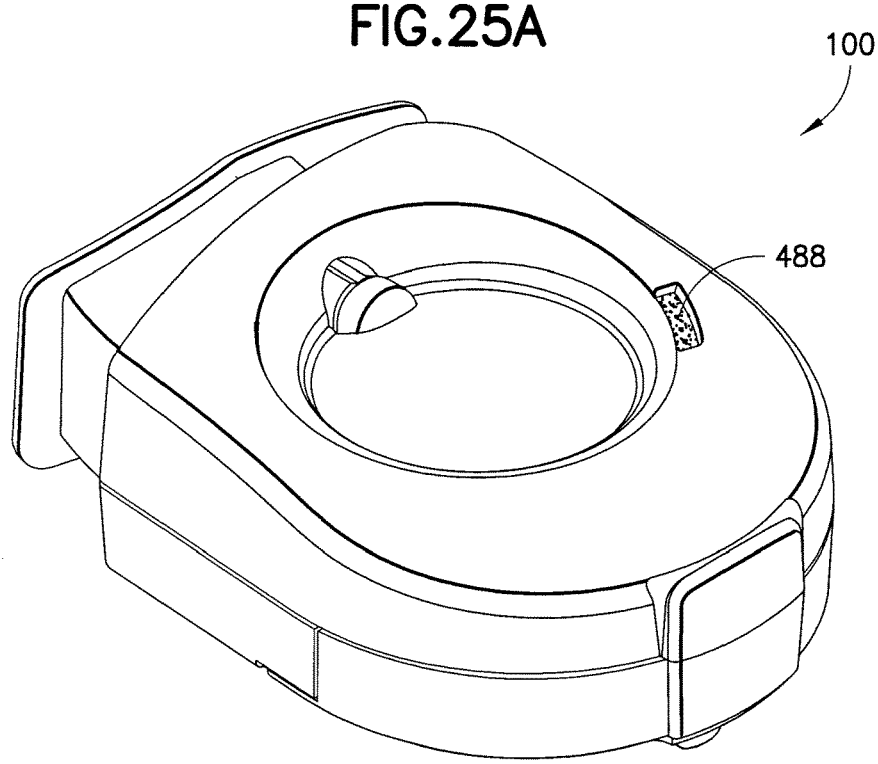

FIGS. 24A and 25A illustrate the infusion device 100 in a pre-activated state. According to one embodiment shown in FIGS. 24A and 25A, the EDI 488 is disposed within the body of the infusion device 100 to be visible from outside the infusion device 100. Additionally, the EDI 488 is disposed such that as the plunger 144 reaches the end of its travel stroke, the foot 212 of the plunger 144 contacts the pressure-sensitive strip 488 due to the force of the pressurization spring 140, and the pressure of the foot 212 against the pressure-sensitive strip 488 induces the color change of the pressure sensitive strip 488. FIGS. 24B and 25B illustrate the infusion device 100 subsequent to foot 212 contacting the pressure-sensitive strip 488 and inducing the color change, thereby indicating completion of the delivery of the medicament.

Figure 26A:
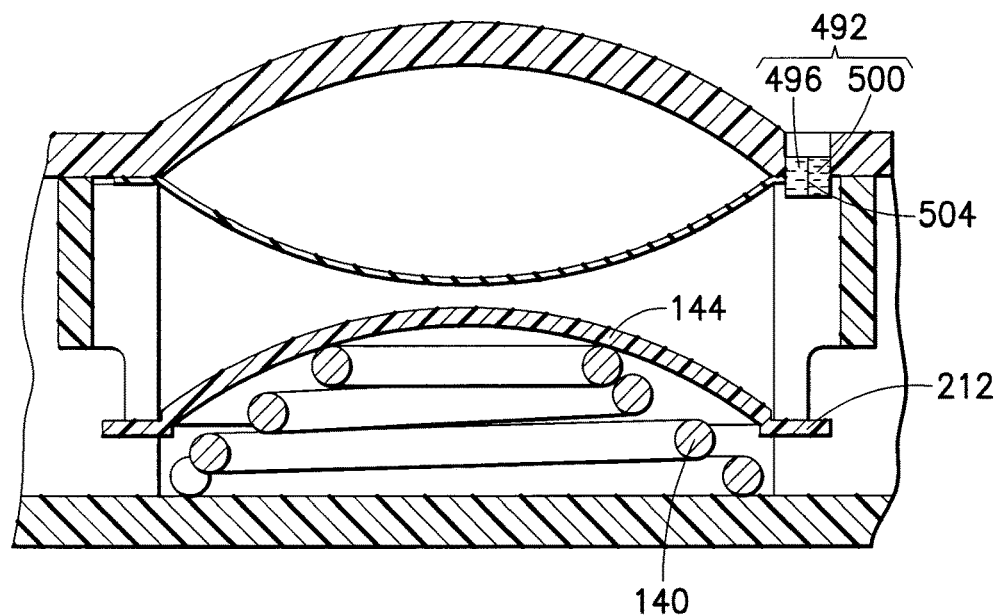
FIGS. 26A and 26B illustrate another end-of-dose indicator and the operation thereof.
Figure 26B:
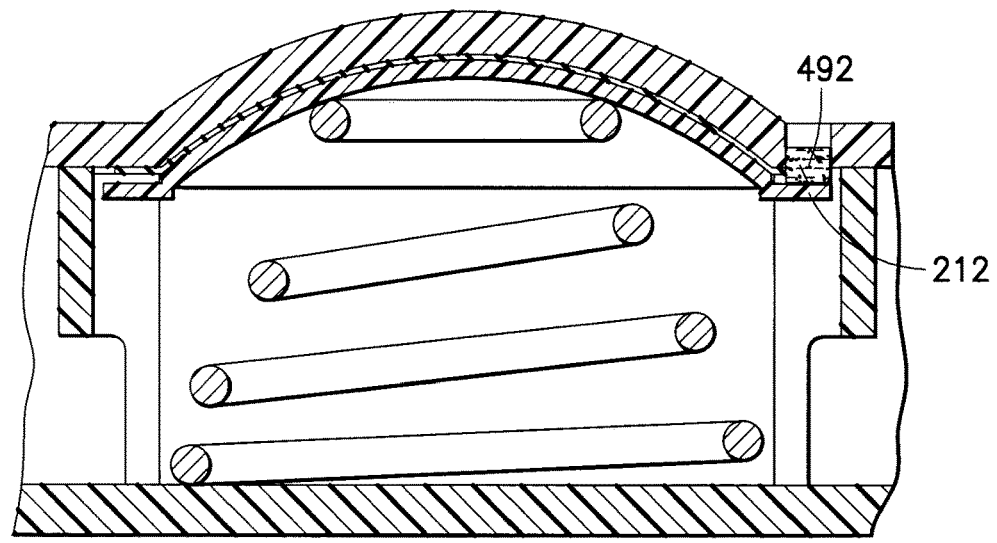

FIGS. 26A and 26B illustrate another end-of-dose indicator (EDI) 492 and the operation thereof. According to one embodiment, the EDI 492 is a dye pack having at least two separated chambers 496 and 500. When the plunger 144 reaches the end of its travel stroke, pressure of the plunger 144 (due to the force of the pressurization spring 140) is imparted to the dye pack 492, rupturing a divider 504 between the two chambers 496 and 500. Once the divider 504 is ruptured, the contents of the two chambers 496 and 500 mix and the mixture changes color, thereby indicating that delivery of the medicament is substantially complete.

According to one embodiment, chamber 496 has a yellow dye and chamber 500 has a blue dye. Once the divider 504 ruptures, the blue and yellow dyes mix and form a green dye, indicating that delivery of the medicament is substantially complete.

According to one embodiment, the EDI 492 is disposed within the reservoir 160, for example, on an interior surface of the transparent dome 176. At the end of the travel stroke of the plunger 144, the pressure of the plunger 144 against the reservoir dome seal 164 is transferred by the reservoir dome seal 164 to the dye pack 492, inducing the color change thereof.

Figure 27A:
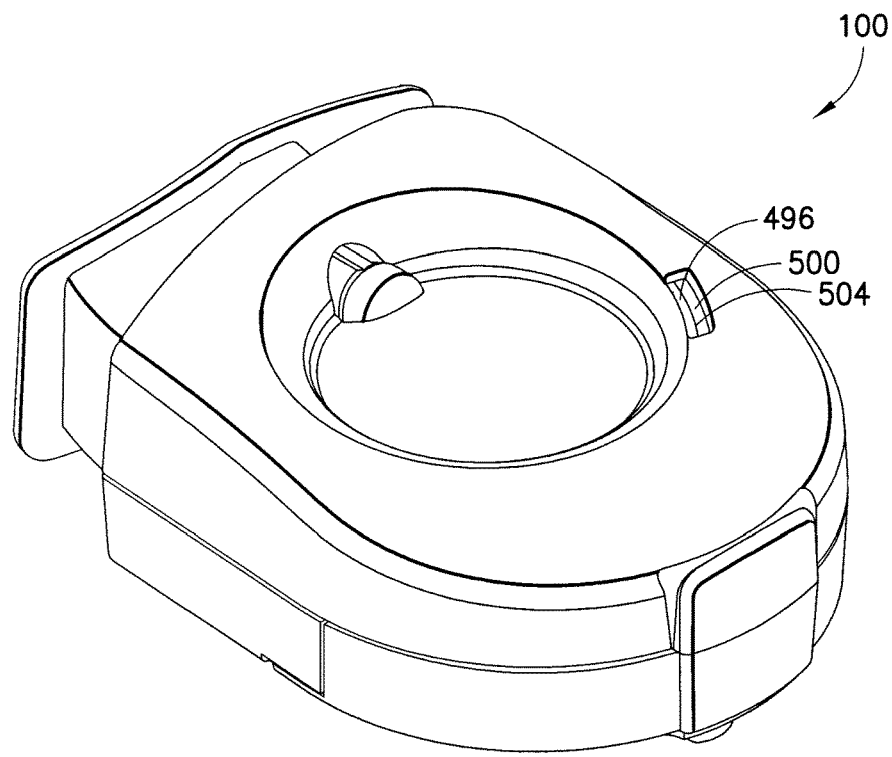
FIGS. 27A and 27B indicate the operation of the end-of-dose indicator of FIG. 26A in the infusion device of FIG. 1.
Figure 27B:
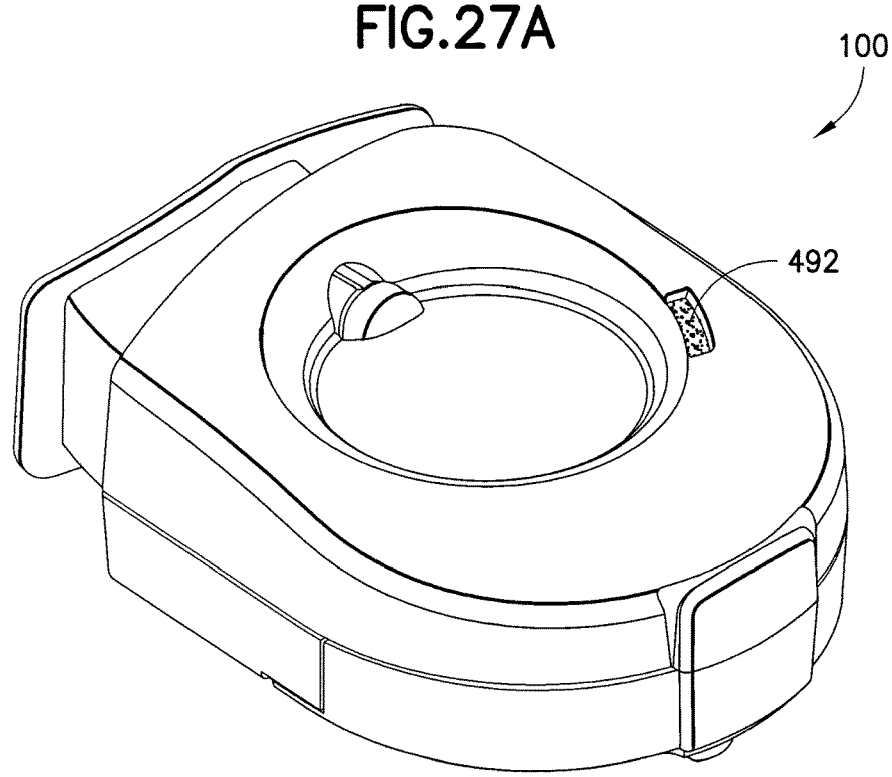

FIGS. 26A and 27A illustrate the infusion device 100 in a pre-activated state. According to one embodiment shown in FIGS. 26A and 27A, the EDI 492 is disposed within the body of the infusion device 100 to be visible from outside the infusion device 100. Additionally, the EDI 492 is disposed such that as the plunger 144 reaches the end of its travel stroke, the foot 212 of the plunger 144 contacts the dye pack 492 due to the force of the pressurization spring 140, and the pressure of the foot 212 against the dye pack 492 ruptures the divider 504 and induces the color change of dye pack. FIGS. 26B and 27B illustrate the infusion device 100 subsequent to foot 212 contacting the dye pack 492 and inducing the color change, thereby indicating completion of the delivery of the medicament.

Figure 28:
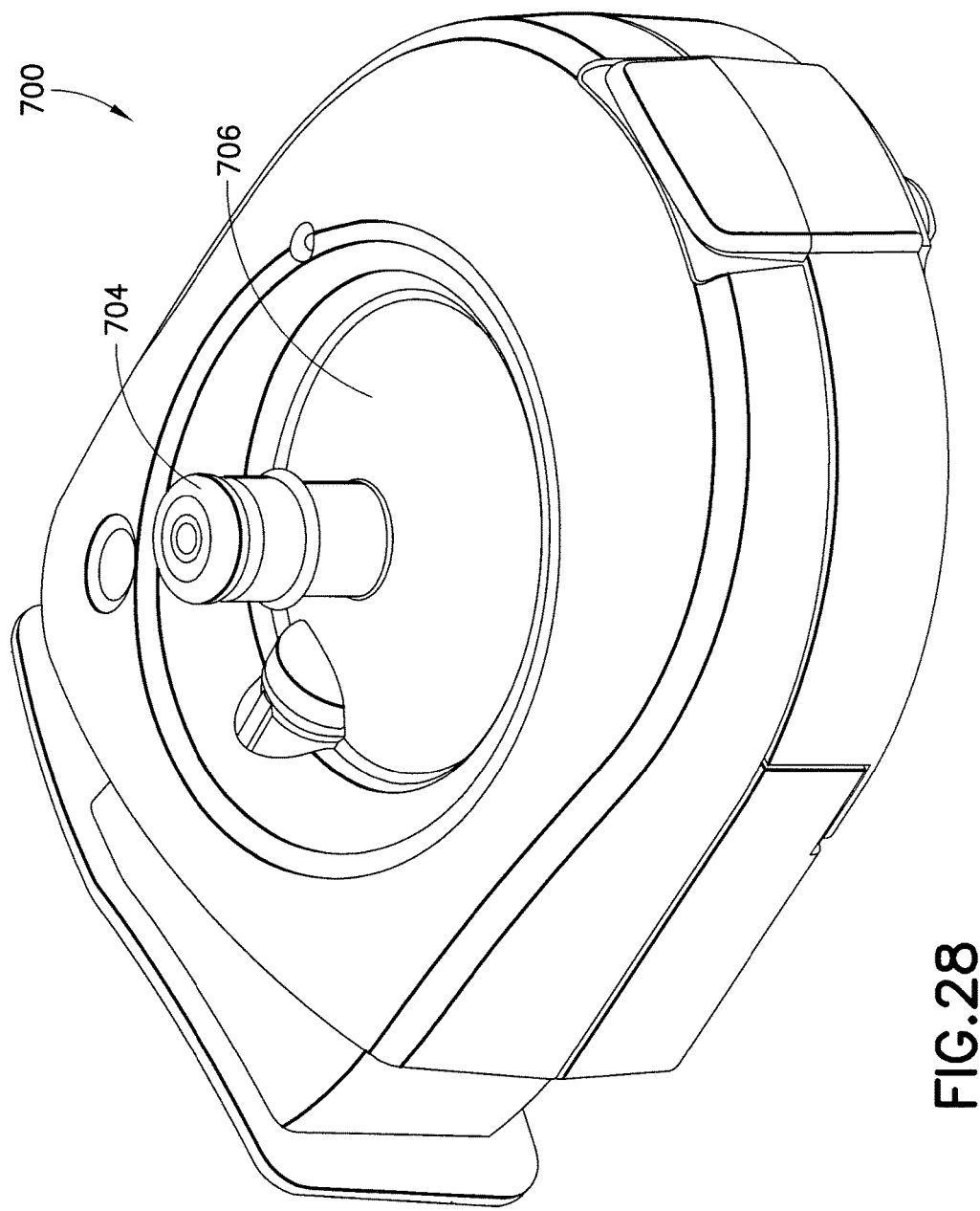
FIG. 28 illustrates an embodiment of an infusion device with an injection port.

FIG. 28 illustrates an embodiment of an infusion device 700 with an injection port 704. The injection port provides access to an evacuated or partially-filled reservoir 708, so that the patient can inject a substance or combination of substances into the reservoir prior to activation. Alternatively, a pharmaceutical manufacturer or pharmacist could employ the injection port 704 to fill the infusion device 700 with a substance or combination of substances prior to sale. In substantially all other respects, the infusion device 700 is similar to the previously-described infusion device 100.

Operation of the infusion device 100 will now be described. The embodiments of the present invention described above preferably include a push-button (activator button 128) design wherein the infusion device 100 can be positioned and affixed to a skin surface, and energized and/or activated by pressing the activator button 128. More specifically, in a first step, the patient removes the device from a sterile packaging (not shown), removes a cover (not shown) of the adhesive pad 264. The patient also removes the needle cover 112. Upon removal of the infusion device 100 from the package and prior to use (see, for example, FIGS. 1, 2, 4, and 5), the infusion device 100 in the pre-activated state allows the patient to inspect both the device and the contents therein, including inspection for missing or damaged components, expiration dates(s), hazy or color-shifted drugs, and so forth.

The next step is the positioning and application of the infusion device 100 to the patient's skin surface. Like a medicinal patch, the patient firmly presses the infusion device 100 onto the skin. One side of the adhesive pad 264 adheres to a bottom surface of the bottom enclosure 104 and a bottom surface of the safety mechanism 108, and the opposing side of the adhesive pad 264 secures the infusion device 100 to the skin of the patient. These bottom surfaces (of the bottom enclosure 104 and the safety mechanism 108) can be flat, contoured, or shaped in any suitable fashion and the adhesive pad 264 is secured thereon. According to one embodiment, prior to shipping, the cover of the adhesive pad 264, such as a film, is applied to the patient-side of the adhesive pad 264 to preserve the adhesive during shipping. As noted above, prior to use, the patient peels back the adhesive cover, thereby exposing the adhesive pad 264 for placement against the skin.

After removing the adhesive cover, the patient is able to place the infusion device 100 against the skin and press to ensure proper adhesion. As noted above, once properly positioned, the device is activated by depressing the activator button 128. This activation step releases plunger 144 and the pressurization spring 140, allowing a plunger 144 to press against the flexible film (reservoir dome seal 164) of the reservoir 160, thereby pressurizing the reservoir. This activation step also serves to release the drive spring 148 from the drive spring holder 260 of the rotor 136, thereby driving the microneedles 152 to extend outside the infusion device 100 (through the opening 300 in the bottom enclosure 104 and the needle opening 156 of the safety mechanism 108) and seat the microneedles 152 within the patient. Further, the activation step opens the valve 168, establishing a fluid communication path between the reservoir 160 and the microneedles 152, via the channel 172 (see, for example, FIGS. 8-10). A significant benefit derives from the ability to achieve each of these actions in a single push-button operation. Additionally, another significant benefit includes the use of a continuous fluid communication path comprised entirely within the reservoir subassembly 120.

Once activated, the patient typically leaves the infusion device 100 in position, or wears the device, for some period of time (such as ten minutes to seventy-two hours) for complete delivery of the reservoir contents. Substantial completion of delivery of the medicament is indicated by the EDI, for example, EDI 124. The patient then removes and discards the device with no damage to the underlying skin or tissue. Upon intentional or accidental removal, one or more safety features deploy to shield the exposed microneedles 152. More specifically, when the infusion device 100 is removed by the patient from the skin, the adhesive pad 264 acts to deploy the safety mechanism 108 from the infusion device 100, thereby shielding the microneedles 152, which otherwise would be exposed upon removal of the infusion device 100 from the patient. When the safety mechanism 108 is fully extended, the safety mechanism 108 locks into place and prevents accidental injury or exposure to the microneedles 152. The safety features, however, can be configured to not deploy if the activator button 128 has not been depressed and the microneedles 152 have not been extended, thereby preventing pre-use safety mechanism deployment. After use, the patient can once again inspect the device to ensure the entire dose was delivered. For example, the patient can view the reservoir interior through the transparent dome 176 and/or inspect the EDI 124.

The described embodiments are suitable for use in administering various substances, including medications and pharmaceutical agents, to a patient, and particularly to a human patient. As used herein, a pharmaceutical agent includes a substance having biological activity that can be delivered through the body membranes and surfaces, and particularly the skin. Examples, listed in greater detail below, include antibiotics, antiviral agents, analgesics, anesthetics, anorexics, antiarthritics, antidepressants, antihistamines, anti-inflammatory agents, antineoplastic agents, vaccines, including DNA vaccines, and the like. Other substances that can be delivered intradermally or subcutaneously to a patient include human growth hormone, insulin, proteins, peptides and fragments thereof. The proteins and peptides can be naturally occurring, synthesized or recombinantly produced. Additionally, the device can be used in cell therapy, as during intradermal infusion of dendritic cells. Still other substances which can be delivered in accordance with the method of the present invention can be selected from the group consisting of drugs, vaccines and the like used in the prevention, diagnosis, alleviation, treatment, or cure of disease, with the drugs including Alpha-1 anti-trypsin, Anti-Angiogenesis agents, Antisense, butorphanol, Calcitonin and analogs, Ceredase, COX-II inhibitors, dermatological agents, dihydroergotamine, Dopamine agonists and antagonists, Enkephalins and other opioid peptides, Epidermal growth factors, Erythropoietin and analogs, Follicle stimulating hormone, G-CSF, Glucagon, GM-CSF, granisetron, Growth hormone and analogs (including growth hormone releasing hormone), Growth hormone antagonists, Hirudin and Hirudin analogs such as hirulog, IgE suppressors, Insulin, insulinotropin and analogs, Insulin-like growth factors, Interferons, Interleukins, Leutenizing hormone, Leutenizing hormone releasing hormone and analogs, Low molecular weight heparin, M-CSF, metoclopramide, Midazolam, Monoclonal antibodies, Narcotic analgesics, nicotine, Non-steroid anti-inflammatory agents, Oligosaccharides, ondansetron, Parathyroid hormone and analogs, Parathyroid hormone antagonists, Prostaglandin antagonists, Prostaglandins, Recombinant soluble receptors, scopolamine, Serotonin agonists and antagonists, Sildenafil, Terbutaline, Thrombolytics, Tissue plasminogen activators, TNF-, and TNF-antagonist, the vaccines, with or without carriers/adjuvants, including prophylactics and therapeutic antigens (including but not limited to subunit protein, peptide and polysaccharide, polysaccharide conjugates, toxoids, genetic based vaccines, live attenuated, reassortant, inactivated, whole cells, viral and bacterial vectors) in connection with, addiction, arthritis, cholera, cocaine addiction, diphtheria, tetanus, HIB, Lyme disease, meningococcus, measles, mumps, rubella, varicella, yellow fever, Respiratory syncytial virus, tick borne japanese encephalitis, pneumococcus, *streptococcus*, typhoid, influenza, hepatitis, including hepatitis A, B, C and E, otitis media, rabies, polio, HIV, parainfluenza, rotavirus, Epstein Barr Virus, CMV, *chlamydia*, non-typeable *haemophilus, moraxella catarrhalis*, human papilloma virus, tuberculosis including BCG gonorrhoea, asthma, ateroschlerosis malaria, *E-coli*, Alzheimers, H. *Pylori, salmonella*, diabetes, cancer, herpes simplex, human papilloma and the like other substances including all of the major therapeutics such as agents for the common cold, Anti-addiction, anti-allergy, anti-emetics, anti-obesity, antiosteoporeteic, anti-infectives, analgesics, anesthetics, anorexics, antiarthritics, antiasthmatic agents, anticonvulsants, anti-depressants, antidiabetic agents, antihistamines, anti-inflammatory agents, antimigraine preparations, antimotion sickness preparations, antinauseants, antineoplastics, antiparkinsonism drugs, antipruritics, antipsychotics, antipyretics, anticholinergics, benzodiazepine antagonists, vasodilators, including general, coronary, peripheral and cerebral, bone stimulating agents, central nervous system stimulants, hormones, hypnotics, immunosuppressives, muscle relaxants, parasympatholytics, parasympathomimetrics, prostaglandins, proteins, peptides, polypeptides and other macromolecules, psychostimulants, sedatives, sexual hypofunction and tranquilizers and major diagnostics such as tuberculin and other hypersensitivity agents as described in U.S. Pat. No. 6,569,143, entitled "Method of Intradermally Injecting Substances", the entire content of which is expressly incorporated herein by reference.

Vaccine formulations which can be delivered in accordance with the system and method of the present invention can be selected from the group consisting of an antigen or antigenic composition capable of eliciting an immune response against a human pathogen, which antigen or antigenic composition is derived from HIV-1, (such as tat, nef, gp120 or gp160), human herpes viruses (HSV), such as gD or derivatives thereof or Immediate Early protein such as ICP27 from HSVI or HSV2, cytomegalovirus (CMV (esp Human) (such as gB or derivatives thereof), Rotavirus (including live-attenuated viruses), Epstein Barr virus (such as gp350 or derivatives thereof), Varicella Zoster Virus (VZV, such as gp1, II and 1E63) or from a hepatitis virus such as hepatitis B virus (for example Hepatitis B Surface antigen or a derivative thereof), hepatitis A virus (HAV), hepatitis C virus and hepatitis E virus, or from other viral pathogens, such as paramyxoviruses: Respiratory Syncytial virus (RSV, such as F and G proteins or derivatives thereof), parainfluenza virus, measles virus, mumps virus, human papilloma viruses (HPV for example HPV6, 11, 16, 18), flaviviruses (e. g. Yellow Fever Virus, Dengue Virus, Tickborne encephalitis virus, Japanese Encephalitis Virus) or Influenza virus (whole live or inactivated virus, split influenza virus, grown in eggs or MDCK cells, or whole flu virosomes or purified or recombinant proteins thereof, such as HA, NP, NA, or M proteins, or combinations thereof), or derived from bacterial pathogens such as *Neisseria* spp, including *N. gonorrhea* and *N. meningitidis* (for example capsular polysaccharides and conjugates thereof, transferrin-binding proteins, lactoferrin binding proteins, PilC, adhesins); *S. pyogenes* (for example M proteins or fragments thereof, C5A protease, lipoteichoic acids), *S. agalactiae, S. mutans; H. ducreyi; Moraxella* spp, including *M catarrhalis*, also known as Branhamella *catarrhalis* (for example high and low molecular weight adhesins and invasins); *Bordetella* spp, including *B. pertussis* (for example pertactin, pertussis toxin or derivatives thereof, filamenteous hemagglutinin, adenylate cyclase, fimbriae), *B. parapertussis* and *B. bronchiseptica; Mycobacterium* spp., including *M. tuberculosis* (for example ESAT6, Antigen 85A, -B or -C), *M. bovis, M. leprae, M. avium, M. paratuberculosis M. smegmatis; Legionella* spp, including *L. pneumophila; Escherichia* spp, including enterotoxic *E. coli* (for example colonization factors, heat-labile toxin or derivatives thereof, heat-stable toxin or derivatives thereof), enterohemorragic *E. coli*, enteropathogenic *E. coli* (for example shiga toxin-like toxin or derivatives thereof); *Vibrio* spp, including *V. cholera* (for example cholera toxin or derivatives thereof); *Shigella* spp, including *S. sonnei, S. dysenteriae, S. flexnerii; Yersinia* spp, including *Y. enterocolitica* (for example a Yop protein), *Y. pestis, Y. pseudotuberculosis; Campylobacter* spp, including *C. jejuni* (for example toxins, adhesins and invasins) and *C. coli; Salmonella* spp, including *S. typhi, S. paratyphi, S. choleraesuis, S. enteritidis; Listeria* spp., including *L. monocytogenes; Helicobacter* spp, including *H. pylori* (for example urease, catalase, vacuolating toxin); *Pseudomonas* spp, including *P. aeruginosa; Staphylococcus* spp., including *S. aureus*, S. *Epidermidis; Enterococcus* spp., including *E. faecalis, E. faecium; Clostridium* spp., including *C. tetani* (for example tetanus toxin and derivative thereof), *C. botulinum* (for example Botulinum toxin and derivative thereof), *C. difficile* (for example *clostridium* toxins A or B and derivatives thereof); *Bacillus* spp., including *B. anthracis* (for example botulinum toxin and derivatives thereof); *Corynebacterium* spp., including *C. diphtheriae* (for example diphtheria toxin and derivatives thereof); *Borrelia* spp., including B. *Burgdorferi* (for example OspA, OspC, DbpA, DbpB), *B. garinii* (for example OspA, OspC, DbpA, DbpB), *B. afzelii* (for example OspA, OspC, DbpA, DbpB), *B. andersonii* (for example OspA, OspC, DbpA, DbpB), B. *Hermsii; Ehrlichia* spp., including *E. equi* and the agent of the Human Granulocytic Ehrlichiosis; *Rickettsia* spp., including *R. rickettsii; Chlamydia* spp., including C. *Trachomatis* (for example MOMP, heparin-binding proteins), *C. pneumoniae* (for example MOMP, heparin-binding proteins), *C. psittaci; Leptospira* spp., including *L. interrogans; Treponema* spp., including *T. pallidum* (for example the rare outer membrane proteins), *T. denticola, T. hyodysenteriae*; or derived from parasites such as *Plasmodium* spp., including *P. Falciparum; Toxoplasma* spp., including *T. gondii* (for example SAG2, SAG3, Tg34); *Entamoeba* spp., including *E. histolytica; Babesia* spp., including *B. microti; Trypanosoma* spp., including *T. cruzi; Giardia* spp., including *G. lamblia; Leshmania* spp., including *L. major; Pneumocystis* spp., including P. *Carinii; Trichomonas* spp., including *T. vaginalis; Schisostoma* spp., including *S. mansoni*, or derived from yeast such as *Candida* spp., including *C. albicans; Cryptococcus* spp., including *C. neoformans*, as described in PCT Patent Publication No. WO 02/083214, entitled "Vaccine Delivery System", the entire content of which is expressly incorporated herein by reference.

These also include other preferred specific antigens for *M. tuberculosis*, for example Tb Ra12, Tb H9, Tb Ra35, Tb38-1, Erd 14, DPV, MTI, MSL, mTTC2 and hTCC1. Proteins for *M. tuberculosis* also include fusion proteins and variants thereof where at least two, preferably three polypeptides of *M. tuberculosis* are fused into a larger protein. Preferred fusions include Ra12-TbH9-Ra35, Erd14-DPV-MTI, DPV-MTI-MSL, Erd14-DPV-MTI-MSL-mTCC2, Erd14-DPV-MTI-MSL, DPV-MTI-MSL-mTCC2, TbH9-DPV-MTI. Most preferred antigens for *Chlamydia* include for example the High Molecular Weight Protein (HWMP), ORF3, and putative membrane proteins (Pmps). Preferred bacterial vaccines comprise antigens derived from *Streptococcus* spp, including *S. pneumoniae* (for example capsular polysaccharides and conjugates thereof, PsaA, PspA, streptolysin, choline-binding proteins) and the protein antigen Pneumolysin (Biochem Biophys Acta, 1989, 67, 1007; Rubins et al., Microbial Pathogenesis, 25, 337-342), and mutant detoxified derivatives thereof. Other preferred bacterial vaccines comprise antigens derived from *Haemophilus* spp., including *H. influenzae* type B ("Hib", for example PRP and conjugates thereof), non typeable *H. influenzae*, for example OMP26, high molecular weight adhesins, P5, P6, protein D and lipoprotein D, and fimbrin and fimbrin derived peptides or multiple copy variants or fusion proteins thereof. Derivatives of Hepatitis B Surface antigen are well known in the art and include, inter alia, PreS1, PreS2 S antigens. In one preferred aspect the vaccine formulation of the invention comprises the HIV-1 antigen, gp120, especially when expressed in CHO cells. In a further embodiment, the vaccine formulation of the invention comprises gD2t as hereinabove defined.

In addition to the delivery of substances listed above, the infusion device 100 can also be used for withdrawing a substance from a patient, or monitoring a level of a substance in the patient. Examples of substances that can be monitored or withdrawn include blood, interstitial fluid or plasma. The withdrawn substances can then be analyzed for analytes, glucose, drugs, and the like.

Although only a few exemplary embodiments of the present invention have been described in detail above, those skilled in the art will readily appreciate that many modifications are possible in the exemplary embodiments without materially departing from the novel teachings and advantages of this invention. Accordingly, all such modifications are intended to be included within the scope of the appended claims and equivalents thereof.

What is claimed is:

1. A drug delivery device, comprising:

a body having a reservoir disposed therein for containing a medicament;

an injection needle for penetrating a patient's skin, the needle being in fluid communication with the reservoir;

a pressurization unit and a plunger movable within the body under a force of the pressurization unit for contacting the reservoir; and an end-of-dose indicator visible outside the device for indicating that delivery of the medicament is substantially complete, the end-of-dose indicator comprising a post rotatably disposed within the body and having a helical face; and wherein the helical face of the post bears against an edge of the plunger such that motion of the plunger rotates the post from an initial position to a second position, indicating that delivery of the medicament is substantially complete.

2. The device according to claim 1, wherein the end-of-dose indicator further comprises:
 an arm extending from an end of the post; and
 a vertical extrusion extending from an end of the arm through the body to be visible from outside the device.

3. The device according to claim 2, wherein the body includes:
 an arcuate opening through which the vertical extrusion extends; and
 a marker disposed adjacent to the opening, indicating a progress of the delivery of the medicament.

4. The device according to claim 1, wherein the pressurization unit comprises a pressurization spring.

5. The device according to claim 1, wherein throughout the motion of the plunger, the end-of-dose indicator bears against the edge of the plunger.

6. The device according to claim 1, wherein the interaction between the helical face and the edge of the plunger during the motion of the plunger induces less than a full rotation of the post.

7. The device according to claim 1, wherein a pitch of the helical face induces less than a full rotation of the post during the motion of the plunger.

8. The device according to claim 1, wherein the interaction between helical face and the edge of the plunger during the motion of the plunger induces at least one full rotation of the post.

9. The device according to claim 1, wherein a pitch of the helical face induces at least one full rotation of the post during the motion of the plunger.

* * * * *